(12) United States Patent
Allen et al.

(10) Patent No.: US 9,593,203 B2
(45) Date of Patent: *Mar. 14, 2017

(54) METAL COMPLEXES

(75) Inventors: Scott D. Allen, Ithaca, NY (US); Jay J. Farmer, Ithaca, NY (US); Gabriel E. Job, Ithaca, NY (US); Anna E. Cherian, Ithaca, NY (US)

(73) Assignee: Novomer, Inc., Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/233,571

(22) PCT Filed: Jul. 18, 2012

(86) PCT No.: PCT/US2012/047140
§ 371 (c)(1),
(2), (4) Date: Jan. 17, 2014

(87) PCT Pub. No.: WO2013/012895
PCT Pub. Date: Jan. 24, 2013

(65) Prior Publication Data
US 2014/0228538 A1  Aug. 14, 2014

Related U.S. Application Data

(60) Provisional application No. 61/509,093, filed on Jul. 18, 2011.

(51) Int. Cl.
C08G 65/00 (2006.01)
C08G 64/34 (2006.01)
C07F 15/06 (2006.01)

(52) U.S. Cl.
CPC ............ *C08G 64/34* (2013.01); *C07F 15/065* (2013.01)

(58) Field of Classification Search
CPC ..... C07F 15/065; C07F 11/005; C08G 65/266
USPC ................................................. 570/183, 187
See application file for complete search history.

(56) References Cited

U.S. PATENT DOCUMENTS

| | | | |
|---|---|---|---|
| 6,046,188 A | 4/2000 | Malfroy-Camine et al. |
| 7,399,822 B2 | 7/2008 | Coates et al. |
| 8,247,520 B2 | 8/2012 | Allen et al. |
| 8,470,956 B2 | 6/2013 | Allen et al. |
| 8,604,155 B2 | 12/2013 | Allen et al. |
| 8,633,123 B2 | 1/2014 | Allen et al. |
| 8,642,771 B2 | 2/2014 | Gridnev |
| 8,859,822 B2 | 10/2014 | Farmer et al. |
| 8,921,508 B2 | 12/2014 | Allen et al. |
| 8,946,109 B2 | 2/2015 | Allen et al. |
| 8,951,930 B2 | 2/2015 | Allen et al. |

(Continued)

FOREIGN PATENT DOCUMENTS

| | | |
|---|---|---|
| CN | 101412809 A | 4/2009 |
| WO | WO-91/14694 A1 | 10/1991 |

(Continued)

OTHER PUBLICATIONS

International Search Report for PCT/US2012/047140 mailed Dec. 12, 2012.

(Continued)

*Primary Examiner* — Shane Fang
(74) *Attorney, Agent, or Firm* — Choate, Hall and Stewart LLP; John P. Rearick; Michael A. Shinall

(57) ABSTRACT

The present invention provides novel metal complexes, methods of making, and methods of using the same.

35 Claims, 7 Drawing Sheets

(56) References Cited

U.S. PATENT DOCUMENTS

| | | |
|---|---|---|
| 8,956,989 B2 | 2/2015 | Allen et al. |
| 2002/0098471 A1 | 7/2002 | Weinberg et al. |
| 2006/0089252 A1 | 4/2006 | Coates et al. |
| 2011/0152497 A1 | 6/2011 | Allen et al. |
| 2011/0319634 A1 | 12/2011 | North |
| 2012/0259112 A1 | 10/2012 | Gridnev |
| 2013/0066044 A1 | 3/2013 | Allen et al. |
| 2013/0144031 A1 | 6/2013 | Allen et al. |
| 2013/0144032 A1 | 6/2013 | Allen et al. |
| 2013/0144033 A1 | 6/2013 | Allen et al. |
| 2013/0172482 A1 | 7/2013 | Allen et al. |
| 2013/0197223 A1 | 8/2013 | Farmer et al. |
| 2013/0244864 A1 | 9/2013 | Allen et al. |
| 2014/0046008 A1 | 2/2014 | Allen et al. |
| 2014/0171617 A1 | 6/2014 | Farmer |
| 2014/0194622 A1 | 7/2014 | Gridnev |
| 2014/0296522 A1 | 10/2014 | Lee et al. |
| 2014/0343246 A1 | 11/2014 | Allen et al. |
| 2015/0011761 A1 | 1/2015 | Farmer et al. |
| 2015/0051369 A1 | 2/2015 | Allen et al. |
| 2015/0232496 A1 | 8/2015 | Job et al. |
| 2015/0252145 A1 | 9/2015 | Allen et al. |
| 2015/0299386 A1 | 10/2015 | Allen et al. |

FOREIGN PATENT DOCUMENTS

| | | |
|---|---|---|
| WO | WO-96/40148 A1 | 12/1996 |
| WO | WO-2007/128968 A1 | 11/2007 |
| WO | WO-2010/022388 A2 | 2/2010 |
| WO | WO-2010/028362 A1 | 3/2010 |
| WO | WO-2010/033703 A1 | 3/2010 |
| WO | WO-2010/147421 A2 | 12/2010 |
| WO | WO-2011/079041 A1 | 6/2011 |
| WO | WO-2011/163133 A1 | 12/2011 |
| WO | WO-2012/027725 A1 | 3/2012 |
| WO | WO-2012/030619 A1 | 3/2012 |
| WO | WO-2012/040454 A2 | 3/2012 |
| WO | WO-2012/158573 A1 | 11/2012 |
| WO | WO-2013/012895 A1 | 1/2013 |
| WO | WO-2013/022932 A1 | 2/2013 |
| WO | WO-2013/055747 A1 | 4/2013 |
| WO | WO-2013/067460 A1 | 5/2013 |
| WO | WO-2013/090276 A1 | 6/2013 |
| WO | WO-2013/096602 A1 | 6/2013 |
| WO | WO-2014/031811 A1 | 2/2014 |

OTHER PUBLICATIONS

European Search Report for EP12814377, 3 pages (mailed Feb. 25, 2015).

Widger, P.C. et al., Isospecific polymerization of racemic epoxides: a catalyst system for the synthesis of highly isotactic polyethers, Chemical Communications, 46(17): 2935-2937 (2010).

International Search Report for PCT/US2013/056102, 3 pages (Jan. 24, 2014).

Ren, W-M. et al., Mechanistic Aspects of the Copolymerization of $CO_2$ with Epoxides Using a Thermally Stable Single-Site Cobalt(III) Catalyst, J. Am. Chem. Soc., 131: 11509-11518 (2009).

Written Opinion for PCT/US2013/056102, 16 pages (Jan. 24, 2014).

Wu, G-P. et al, Highly Selective Synthesis of $CO_2$ Copolymer from Styrene Oxide, Macromolecules, 43: 9202-9204 (2010).

U.S. Appl. No. 15/155,305, filed May 16, 2016, Farmer et al.

United States Patent No. 9,593,203 B2

METAL COMPLEXES

CROSS REFERENCE TO RELATED APPLICATIONS

The present application claims priority to U.S. provisional patent application Ser. No. 61/509,093, filed Jul. 18, 2011, the entire contents of which are hereby incorporated by reference.

GOVERNMENT SUPPORT

The invention was made in part with United States Government support under grants DE-FE0002474 awarded by the Department of Energy. The United States Government has certain rights in the invention.

BACKGROUND OF THE INVENTION

A variety of different metal complexes have shown utility in effecting the copolymerization of epoxides and carbon dioxide to form aliphatic polycarbonates (APCs), including complexes based on zinc or aluminum salts, double metal cyanide complexes, and more recently, those based on transition metal coordination complexes (e.g., porphyrin complexes, salen complexes, etc.). The latter type provides several advantages, including the production of polycarbonates having a high carbonate content, easier catalyst preparation, and decreased induction time prior to polymerization. However, some of these catalysts have a tendency to become bound to the polymer chain during polymerization, which can complicate separation of the catalyst from the polymer product. Therefore, there remains a need for the continued development of novel metal complexes that have improved reaction and/or product purity characteristics.

SUMMARY OF THE INVENTION

The present invention provides, among other things, metallosalenate complexes comprising a cationic bicyclic guanidinium group, wherein the cationic bicyclic guanidinium group has no free amines. In some embodiments, such metallosalenate complexes are of formula I:

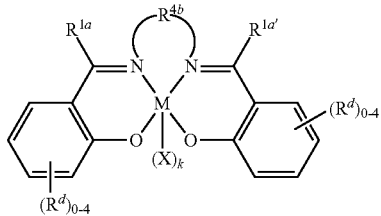

I wherein each of $R^{1a}$, $R^{1a'}$, $R^d$, $R^{4b}$, k, M, and X is as described herein.

DEFINITIONS

Figure 1:
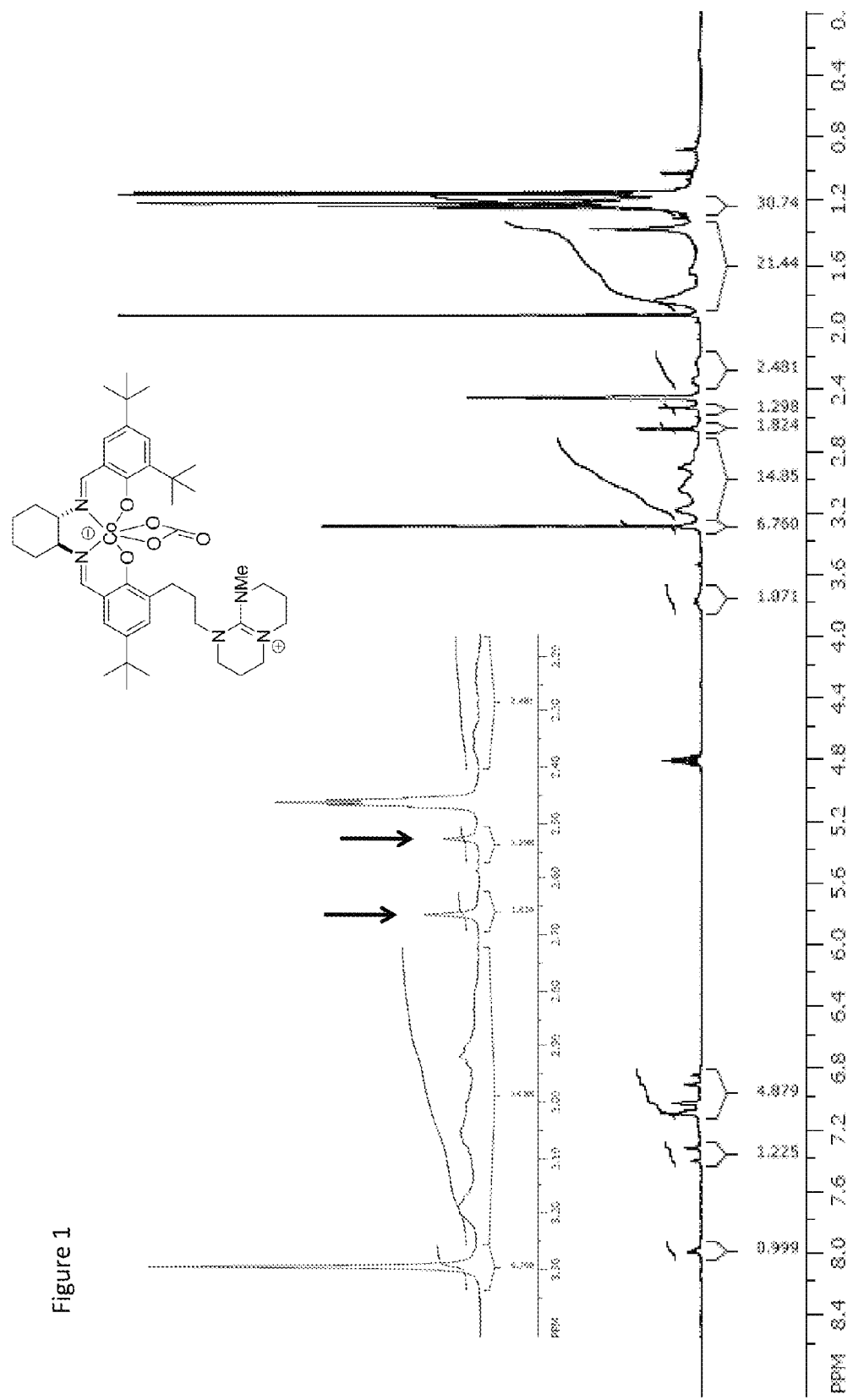
FIG. 1 is a $^1$H-NMR spectrum of a compound of formula I.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound or polymer is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "epoxide", as used herein, refers to a substituted or unsubstituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of substantially alternating units derived from $CO_2$ and an epoxide (e.g., poly(ethylene carbonate). In certain embodiments, a polymer of the present invention is a copolymer, terpolymer, heteropolymer, block copolymer, or tapered heteropolymer incorporating two or more different epoxide monomers.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-40 carbon atoms. In certain embodiments, aliphatic groups contain 1-20 carbon atoms. In certain embodiments, aliphatic groups contain 3-20 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in some embodiments aliphatic groups contain 1-3 carbon atoms, and in some embodiments aliphatic groups contain 1 or 2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, or phosphorus. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and include saturated, unsaturated or partially unsaturated groups.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, the term "3- to 7-membered carbocycle" refers to a 3- to 7-membered saturated or partially unsaturated monocyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in some embodiments alkyl groups contain 1-3 carbon atoms, and in some embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in some embodiments alkenyl groups contain 2-3 carbon atoms, and in some embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in some embodiments alkynyl groups contain 2-3 carbon atoms, and in some embodiments alkynyl groups contain 2 carbon atoms. Representative alkynyl groups include, but are not limited to, ethynyl, 2-propynyl (propargyl), 1-propynyl, and the like.

The term "alkoxy", as used herein refers to an alkyl group, as previously defined, attached to the parent molecule through an oxygen atom. Examples of alkoxy, include but are not limited to, methoxy, ethoxy, propoxy, isopropoxy, n-butoxy, tert-butoxy, neopentoxy, and n-hexoxy.

The term "acyl", as used herein, refers to a carbonyl-containing functionality, e.g., —C(=O)R', wherein R' is hydrogen or an optionally substituted aliphatic, heteroaliphatic, heterocyclic, aryl, heteroaryl group, or is a substituted (e.g., with hydrogen or aliphatic, heteroaliphatic, aryl, or heteroaryl moieties) oxygen or nitrogen containing functionality (e.g., forming a carboxylic acid, ester, or amide functionality). The term "acyloxy", as used here, refers to an acyl group attached to the parent molecule through an oxygen atom.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the term "6- to 10-membered aryl" refers to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7-14-membered polycyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O—(CH$_2$)$_{0-1}$Ph which may be substituted with R$^\circ$; —CH=CHPh, which may be substituted with R$^\circ$; —NO$_2$; —CN; —N$_3$; —(CH$_2$)$_{0-4}$N(R$^\circ$)$_2$; —(CH$_2$)$_{0-4}$N (R$^{\circ}$)C(O)R$^{\circ}$; —N(R$^{\circ}$)C(S)R$^{\circ}$; —(CH$_2$)$_{0-4}$N(R$^{\circ}$)C(O)NR$^{\circ}$$_2$; —N(R$^{\circ}$)C(S)NR$^{\circ}$$_2$; —(CH$_2$)$_{0-4}$N(R$^{\circ}$)C(O)OR$^{\circ}$; —N(R$^{\circ}$)N(R$^{\circ}$)C(O)R$^{\circ}$; —N(R$^{\circ}$)N(R$^{\circ}$)C(O)NR$^{\circ}$$_2$; —N(R$^{\circ}$)N(R$^{\circ}$)C(O)OR$^{\circ}$; —(CH$_2$)$_{0-4}$C(O)R$^{\circ}$; —C(S)R$^{\circ}$; —(CH$_2$)$_{0-4}$C(O)OR$^{\circ}$; —(CH$_2$)$_{0-4}$C(O)N(R$^{\circ}$)$_2$; —(CH$_2$)$_{0-4}$C(O)SR$^{\circ}$; —(CH$_2$)$_{0-4}$C(O)OSiR$^{\circ}$$_3$; —(CH$_2$)$_{0-4}$OC(O)R$^{\circ}$; —OC(O)(CH$_2$)$_{0-4}$SR—, SC(S)SR$^{\circ}$; —(CH$_2$)$_{0-4}$SC(O)R$^{\circ}$; —(CH$_2$)$_{0-4}$C(O)NR$^{\circ}$$_2$; —C(S)NR$^{\circ}$$_2$; —C(S)SR$^{\circ}$; —SC(S)SR$^{\circ}$, —(CH$_2$)$_{0-4}$OC(O)NR$^{\circ}$$_2$; —C(O)N(OR$^{\circ}$)R$^{\circ}$; —C(O)C(O)R$^{\circ}$; —C(O)CH$_2$C(O)R$^{\circ}$; —C(NOR$^{\circ}$)R$^{\circ}$; —(CH$_2$)$_{0-4}$SSR$^{\circ}$; —(CH$_2$)$_{0-4}$S(O)$_2$R$^{\circ}$; —(CH$_2$)$_{0-4}$S(O)$_2$OR$^{\circ}$; —(CH$_2$)$_{0-4}$OS(O)$_2$R$^{\circ}$; —S(O)$_2$NR$^{\circ}$$_2$; —(CH$_2$)$_{0-4}$S(O)R$^{\circ}$; —N(R$^{\circ}$)S(O)$_2$NR$^{\circ}$$_2$; —N(R$^{\circ}$)S(O)$_2$R$^{\circ}$; —N(OR$^{\circ}$)R$^{\circ}$; —C(NH)NR$^{\circ}$$_2$; —P(O)$_2$R$^{\circ}$; —P(O)R$^{\circ}$$_2$; —OP(O)R$^{\circ}$$_2$; —OP(O)(OR$^{\circ}$)$_2$; SiR$^{\circ}$$_3$; —(C$_{1-4}$ straight or branched alkylene)O—N(R$^{\circ}$)$_2$; or —(C$_{1-4}$ straight or branched alkylene)C(O)O—N(R$^{\circ}$)$_2$, wherein each R$^{\circ}$ may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R$^{\circ}$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R$^{\circ}$ (or the ring formed by taking two independent occurrences of R$^{\circ}$ together with their intervening atoms), are independently halogen, —(CH$_2$)$_{0-2}$R$^{\bullet}$, -(haloR$^{\bullet}$), —(CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-4}$C(O)N(R$^{\circ}$)$_2$; —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$ wherein each R$^{\bullet}$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^{\circ}$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^{\dagger}$, —NR$^{\dagger}$$_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, or —N(R$^{\dagger}$)S(O)$_2$R$^{\dagger}$; wherein each R$^{\dagger}$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three R$^{\dagger}$ substituents to provide a charged ammonium moiety —N$^{+}$(R$^{\dagger}$)$_3$, wherein the ammonium moiety is further complexed with a suitable counterion.

Suitable substituents on the aliphatic group of R$^{\dagger}$ are independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

When substituents are described herein, the term "radical" or "optionally substituted radical" is sometimes used. In this context, "radical" means a moiety or functional group having an available position for attachment to the structure on which the substituent is bound. In general the point of attachment would bear a hydrogen atom if the substituent were an independent neutral molecule rather than a substituent. The terms "radical" or "optionally-substituted radical" in this context are thus interchangeable with "group" or "optionally-substituted group".

As used herein, a substance and/or entity is "pure" if it is substantially free of other components. Such relative assessments of components can be determined by molar ratio, dry weight, volume, various analytical techniques (e.g., photometry, spectrometry, spectrophotometry, spectroscopy), etc. In some embodiments, a preparation that contains more than about 75% of a particular substance and/or entity is considered to be a pure preparation. In some embodiments, a substance and/or entity is at least 80%, 85%, 90%, 91%, 92%, 93%, 94%, 95%, 96%, 97%, 98%, or 99% pure.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, about 95%, about 99% or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure.

As used herein, the term "catalyst" refers to a substance the presence of which increases the rate and/or extent of a chemical reaction, while not being consumed or undergoing a permanent chemical change itself.

DETAILED DESCRIPTION OF CERTAIN EMBODIMENTS

The present invention encompasses the recognition that there remains a need for metal complexes that have improved reaction and/or product purity characteristics. The present invention provides, among other things, new metal complexes that do not form permanent covalent bonds with the polymer product. Thus, the present invention provides metal complexes that, compared to certain known metal complexes, are more easily separated from the polymerization product.

Certain transition metal complexes having a salen-type ligand and a tethered bicyclic guanidine group have been shown to be superior catalysts for the copolymerization of epoxides and carbon dioxide (WO2010/022388). It has been observed by Applicant and others that such complexes, or portions thereof, have a tendency to form covalent bonds with the polymer chain during polymerization, complicating purification of the polymer product. While not wishing to be bound by any particular theory, Applicant proposes the possibility that when a bicyclic guanidine moiety, including but not limited to 1,5,7-triazabicyclo[4.4.0]dec-5-ene (TBD), is tethered to the metal complex, the remaining secondary amine group of the bicyclic guanidine group can form a covalent bond with the polymer chain. One possibility of a resulting covalently bound complex is:

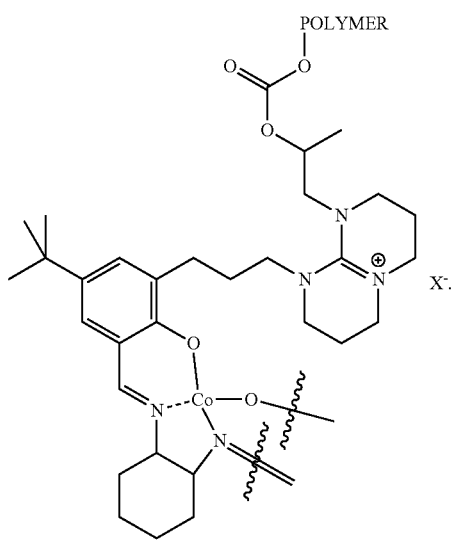

Applicant has also observed that upon quenching certain polymerization processes (e.g., those catalyzed by a metal complex having a secondary amine group) and treating with sulfonic acid ion exchange resins, catalyst fragments may be bound to the polymer chain. Such bound fragments may impart undesirable characteristics to the polymer composition, including but not limited to a yellowing in color. In some embodiments, such bound fragments are portions of the metal complex ligands. One possible depiction of such a bound ligand fragment is:

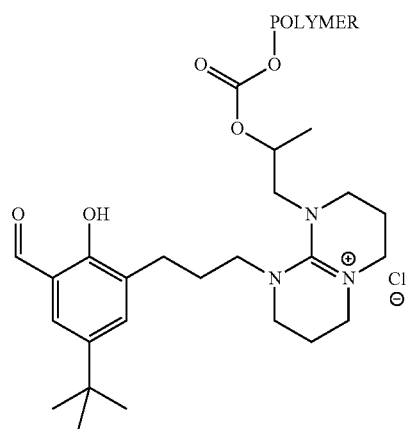

Applicant describes herein that substitution of the secondary amine group prevents the undesirable covalent binding of the metal complex (or fragmented ligand thereof) to the polymer. The present invention therefore provides, in some embodiments, the identification of the previously unknown source of a problem.

Prior to the teachings described herein, those of ordinary skill in the art understood that metal catalysts containing a tethered TBD moiety offered certain advantages for the synthesis of polycarbonates. Against this backdrop, the present disclosure presents surprising evidence of the usefulness and effectiveness of modifying the TBD moiety, or other cationic bicyclic guanidinium group, such that covalent binding to the polymer is prevented.

The present invention provides, among other things, methods for polymerizing an epoxide and carbon dioxide with a provided metal complex to form a polycarbonate polymer composition, wherein the polycarbonate polymer composition is substantially free of covalently-bound metal complex or any guanidine-containing portion thereof. In some embodiments, chromatography is used to obtain an isolated polycarbonate polymer composition. In some embodiments, the isolated polycarbonate polymer composition is substantially free of the metal complex or any guanidine-containing portion thereof.

The present invention encompasses the recognition that polymer-bound versions of the metallosalenate complexes provided herein can be useful. In some embodiments, the present invention provides a metallosalenate complex of formula I, wherein the metallosalenate complex is covalently bound to a polymer chain via a nitrogen atom on a guanidine moiety. In some embodiments, such metallosalenate complexes are solid-phase catalysts.

The present invention provides, among other things, methods for obtaining substantially isolated, intact metal complexes of the present invention following polymerization of an epoxide and carbon dioxide with a provided metal complex.

In some embodiments, the present invention provides a metallosalenate complex comprising a cationic bicyclic guanidinium group, wherein the cationic bicyclic guanidinium group has no free amines. The term "no free amines", as used herein, refers to a guanidinium group having no nitrogen atoms bearing a hydrogen in any tautomeric or resonance form. In some embodiments, a guanidinium group having no nitrogen atoms has two nitrogen atoms each bearing three nonhydrogen substituents and a third nitrogen atom with bonds to four nonhydrogen substituents. In some embodiments, such nonhydrogen substituents are aliphatic substituents. In some embodiments, a guanidinium group having no free amines is cationic, as compared to a neutral guanidinium group having a free amine.

It will be appreciated that when a guanidinium cation is drawn in a particular fashion herein, all resonance or tautomeric forms are contemplated and encompassed by the present disclosure. For example, the group:

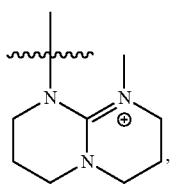 [SMILES: *N1CCCN2CCC[N+](C)=C12]

may also be depicted as

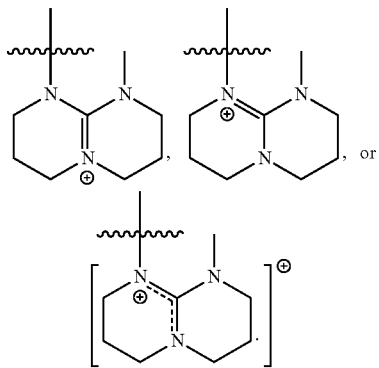

In some embodiments, the present invention provides a metallosalenate complex of formula I:

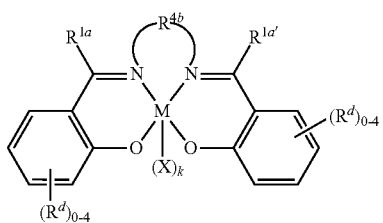

wherein,
$R^{1a}$ and $R^{1a'}$ are independently a hydrogen or an optionally substituted radical selected from the group consisting of $C_{1-12}$ aliphatic; $C_{1-12}$ heteroaliphatic; phenyl; a 3- to 8-membered saturated or partially unsaturated monocyclic carbocycle, a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur;
each $R^d$ is independently a -L-CG group, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more $R^d$ groups may be taken together with intervening atoms to form one or more optionally substituted rings optionally containing one or more heteroatoms, wherein at least one occurrence of $R^d$ is a -L-CG group;

each L is independently a covalent bond or an optionally substituted, saturated or unsaturated, straight or branched, bivalent $C_{1-12}$ hydrocarbon chain, wherein one or more methylene units of L are optionally and independently replaced by -Cy-, —CR$_2$—, —NR—, —N(R)C(O)—, —C(O)N(R)—, —N(R)SO$_2$—, —SO$_2$N(R)—, —O—, —C(O)—, —OC(O)—, —OC(O)O—, —C(O)O—, —N(R)C(O)O—, —SiR$_2$—, —S—, —SO—, or —SO$_2$—;

each CG is independently a cationic bicyclic guanidinium group having no free amines;

each Cy is independently an optionally substituted bivalent ring selected from phenylene, a 3-7 membered saturated or partially unsaturated carbocyclylene, a 3-7 membered saturated or partially unsaturated monocyclic heterocyclylene having 1-2 heteroatoms independently selected from nitrogen, oxygen, or sulfur, or a 5-6 membered heteroarylene having 1-3 heteroatoms independently selected from nitrogen, oxygen;

$R^{4b}$ is selected from the group consisting of:

a)

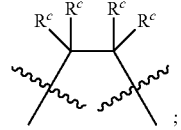

b)

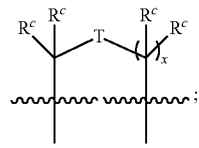

c)

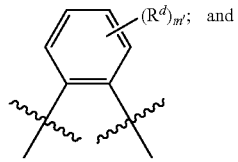 and d)

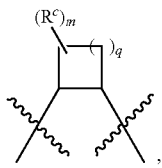

where
R$^c$ at each occurrence is independently hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R$^c$ groups may be taken together with the carbon atoms to which they are attached and any intervening atoms to form one or more optionally substituted rings;

R at each occurrence is independently hydrogen, an optionally substituted radical selected the group consisting of acyl; C$_{1-20}$ aliphatic; C$_{1-20}$ heteroaliphatic; carbamoyl; arylalkyl; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring;

T is a divalent linker selected from the group consisting of: —NR—, —N(R)C(O)—, —C(O)NR—, —O—, —C(O)—, —OC(O)—, —C(O)O—, —S—, —SO—, —SO$_2$—, —SiR$_2$—, —C(=S)—, —C(=NR)—, or —N=N—; a polyether; a C$_3$ to C$_8$ substituted or unsubstituted carbocycle; and a C$_1$ to C$_8$ substituted or unsubstituted heterocycle;

M is a metal atom;
each X is independently a suitable counterion;
k is from 0 to 2, inclusive;
m is from 0 to 6, inclusive;
m' is from 0 to 4, inclusive;
q is from 0 to 4, inclusive; and
x is from 0 to 2, inclusive.

In certain embodiments, the present invention provides a metallosalenate complex of formula II:

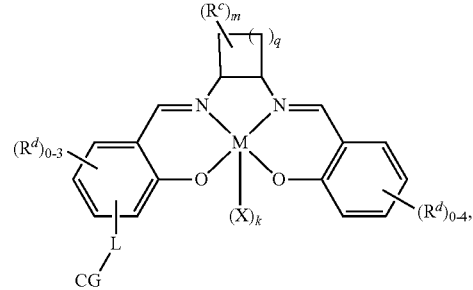

II wherein each of k, m, q, L, CG, R$^c$, R$^d$, M, and X are as defined above and described in classes and subclasses herein, both singly and in combination.

In certain embodiments, the present invention provides a metallosalenate complex of formula II-a:

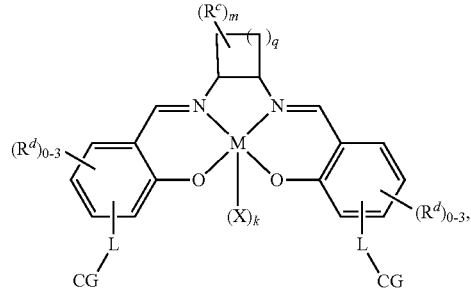

II-a wherein each of k, m, q, L, CG, R$^c$, R$^d$, M, and X are as defined above and described in classes and subclasses herein, both singly and in combination.

In certain embodiments, the present invention provides a metallosalenate complex of formula II-aa, II-bb, II-cc, II-dd, II-ee, II-ff, II-gg, or II-hh:

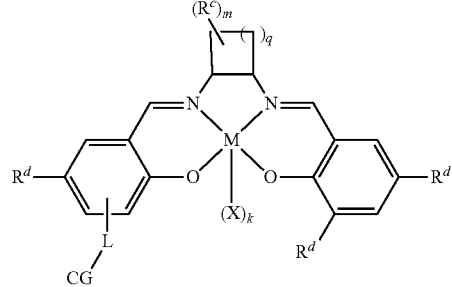

II-aa

II-bb

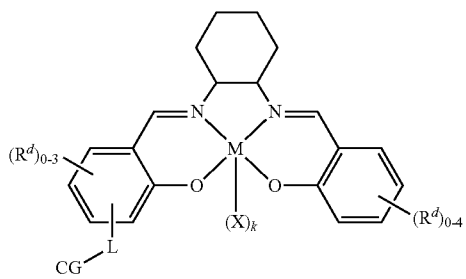

II-cc

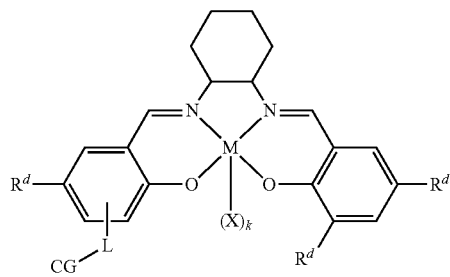

II-dd

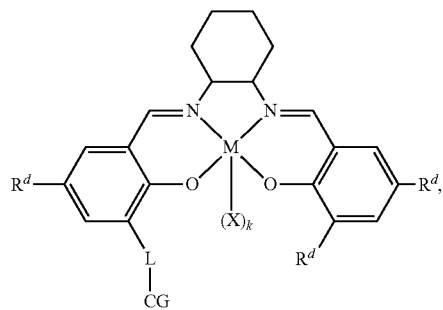

II-ee

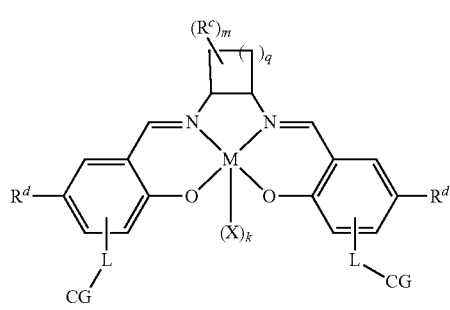

II-ff

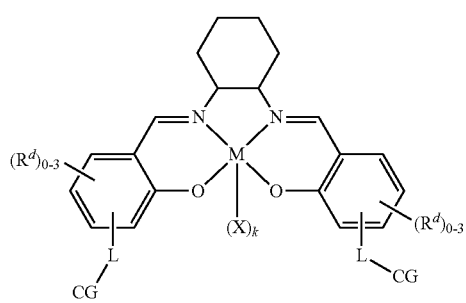

II-gg

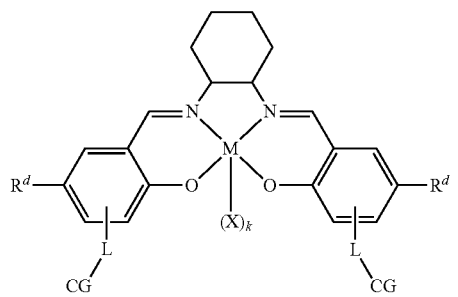

II-hh

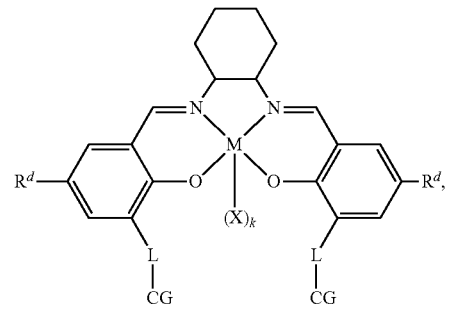

wherein each of k, m, q, L, CG, $R^c$, $R^d$, M, and X are as defined above and described in classes and subclasses herein, both singly and in combination.

In certain embodiments, the present invention provides a metallosalenate complex of formula III:

III

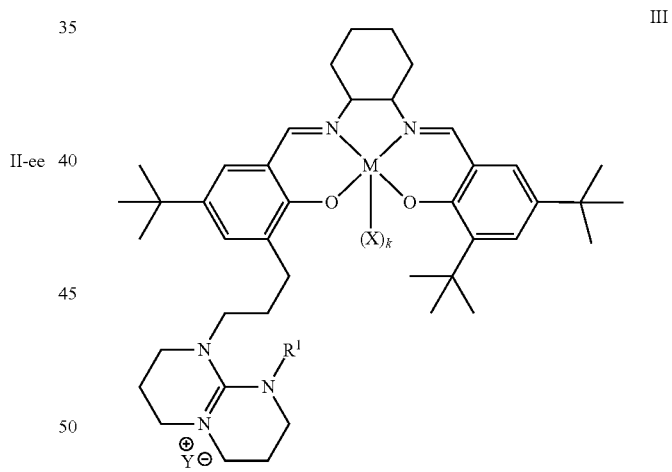

wherein each of k, M, and X are as defined above and described in classes and subclasses herein, both singly and in combination;

$R^1$ is —S(O)R, —S(O)$_2$R, —CO$_2$R, —C(O)R, —C(O)NR$_2$, —C(O)SR, or R;

each R is independently an optionally substituted moiety selected from the group consisting of $C_{1-20}$ aliphatic; $C_{1-20}$ heteroaliphatic; 3- to 8-membered saturated or partially unsaturated monocyclic carbocycle; a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring; and Y, when present, is a suitable counterion;
  wherein when k is 2, Y is absent and X comprises two monodentate moieties or a single bidentate moiety, or X and Y are taken together to comprise a suitable dianion.

In some embodiments, the present invention provides a metallosalenate complex of formula III-a:

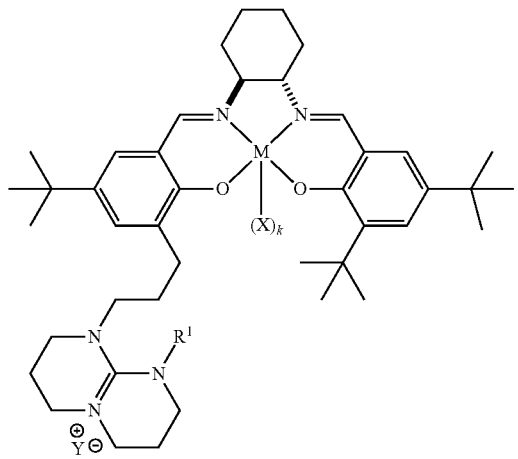

III-a wherein each of k, M, X, Y, and $R^1$ are as defined above and described in classes and subclasses herein, both singly and in combination.

In certain embodiments, the present invention provides a metallosalenate complex of formula IV:

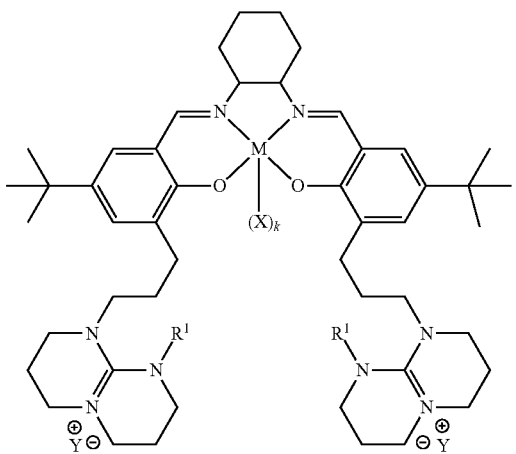

IV wherein each of k, M, X, Y, and $R^1$ are as defined above and described in classes and subclasses herein, both singly and in combination.

In certain embodiments, the present invention provides a metallosalenate complex of formula IV-a:

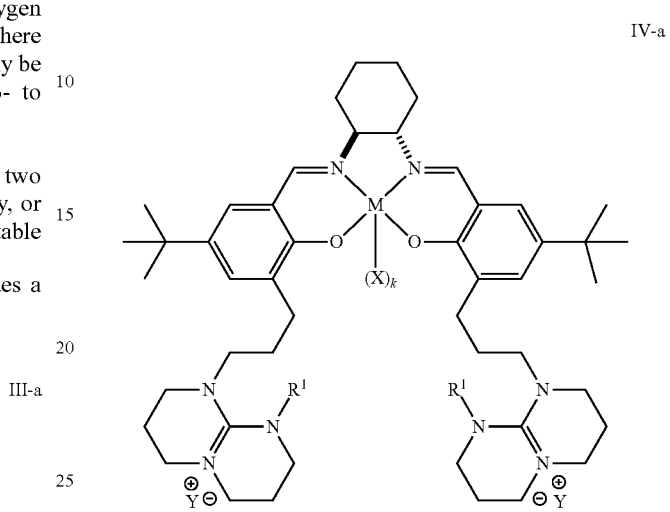

IV-a wherein each of k, M, X, Y, and $R^1$ are as defined above and described in classes and subclasses herein, both singly and in combination.

In some embodiments, a metal atom, M, is selected from periodic table groups 3-13, inclusive. In certain embodiments, M is a transition metal selected from periodic table groups 5-12, inclusive. In some embodiments, M is a transition metal selected from periodic table groups 4-11, inclusive. In certain embodiments, M is a transition metal selected from periodic table groups 5-10, inclusive. In certain embodiments, M is a transition metal selected from periodic table groups 7-9, inclusive. In some embodiments, M is selected from the group consisting of Cr, Mn, V, Fe, Co, Mo, W, Ru, Al, and Ni. In some embodiments, M is a metal atom selected from the group consisting of: cobalt; chromium; aluminum; titanium; ruthenium, and manganese. In some embodiments, M is cobalt. In some embodiments, M is chromium. In some embodiments, M is aluminum. In certain embodiments where a metallosalenate complex is a cobalt complex, the cobalt metal has an oxidation state of +3 (i.e., Co(III)). In other embodiments, the cobalt metal has an oxidation state of +2 (i.e., Co(II)).

In some embodiments $R^{1a}$ and $R^{1a'}$ are hydrogen.

In some embodiments, one occurrence of $R^d$ is a -L-CG group, and any other $R^d$ groups are optionally substituted $C_{1-20}$ aliphatic groups or an optionally substituted phenyl group.

In some embodiments, two occurrences of $R^d$ are a -L-CG group, and any other $R^d$ groups are optionally substituted $C_{1-20}$ aliphatic groups or an optionally substituted phenyl group. In certain embodiments, the two -L-CG groups are appended to the same salicylaldehyde aryl ring. In certain embodiments, the two -L-CG groups are to different salicylaldehyde aryl rings. In certain embodiments, the two -L-CG groups are appended to different salicylaldehyde aryl rings such that the resulting complex is C2-symmetric. In some embodiments, where a metal complex has multiple -L-CG groups, each -L-CG group is the same. In some embodiments, where a metal complex has multiple -L-CG groups, at least one -L-CG group is different from other -L-CG groups.

In certain embodiments, -L- is an optionally substituted, saturated or unsaturated, straight or branched, bivalent $C_{1-2}$ hydrocarbon chain, wherein one, two, or three methylene units of L are optionally and independently replaced by -Cy-, —$CR_2$—, —NR—, —N(R)C(O)—, —C(O)N(R)—, —N(R)SO$_2$—, —SO$_2$N(R)—, —O—, —C(O)—, —OC(O)—, —OC(O)O—, —C(O)O—, —N(R)C(O)O—, —SiR$_2$—, —S—, —SO—, or —SO$_2$—. In certain embodiments, -L- is an optionally substituted, saturated or unsaturated, straight or branched, bivalent $C_{1-6}$ hydrocarbon chain, wherein one, two, or three methylene units of L are optionally and independently replaced by -Cy-, —$CR_2$—, —NR—, —N(R)C(O)—, —C(O)N(R)—, —N(R)SO$_2$—, —SO$_2$N(R)—, —O—, —C(O)—, —OC(O)—, —OC(O)O—, —C(O)O—, —N(R)C(O)O—, —SiR$_2$—, —S—, —SO—, or —SO$_2$—. In some embodiments, -L- is an optionally substituted, saturated or unsaturated, straight or branched, bivalent $C_{1-6}$ hydrocarbon chain, wherein one or two methylene units of L are optionally and independently replaced by —NR—, —O—, or —C(O)—.

In some embodiments, -L- is a straight or branched, saturated or unsaturated, bivalent $C_{1-12}$ hydrocarbon chain. In some embodiments, -L- is a straight or branched, saturated or unsaturated, bivalent $C_{1-6}$ hydrocarbon chain. In some embodiments, -L- is —(CH$_2$)$_6$—. In some embodiments, -L- is —(CH$_2$)$_5$—. In some embodiments, -L- is —(CH$_2$)$_4$—. In some embodiments, -L- is —(CH$_2$)$_3$—. In some embodiments, -L- is —(CH$_2$)$_2$—. In some embodiments, -L- is —(CH$_2$)—.

In some embodiments, -L- is selected from the group consisting of:

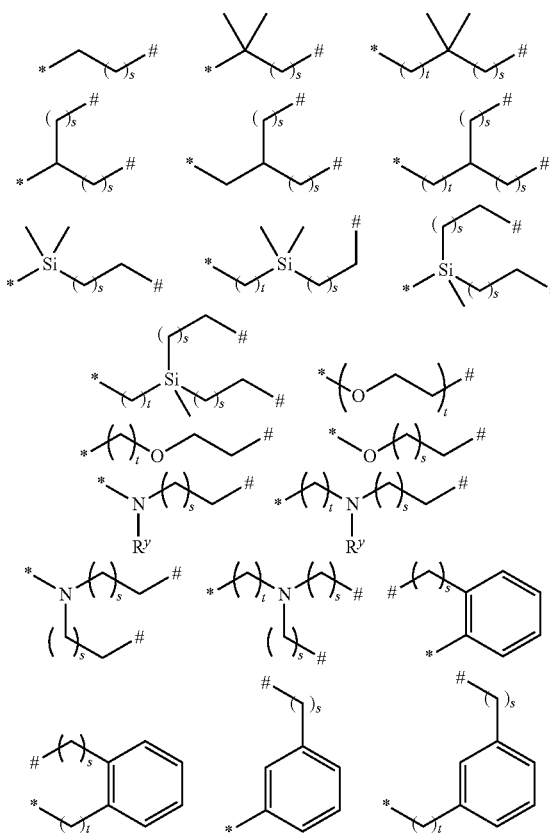

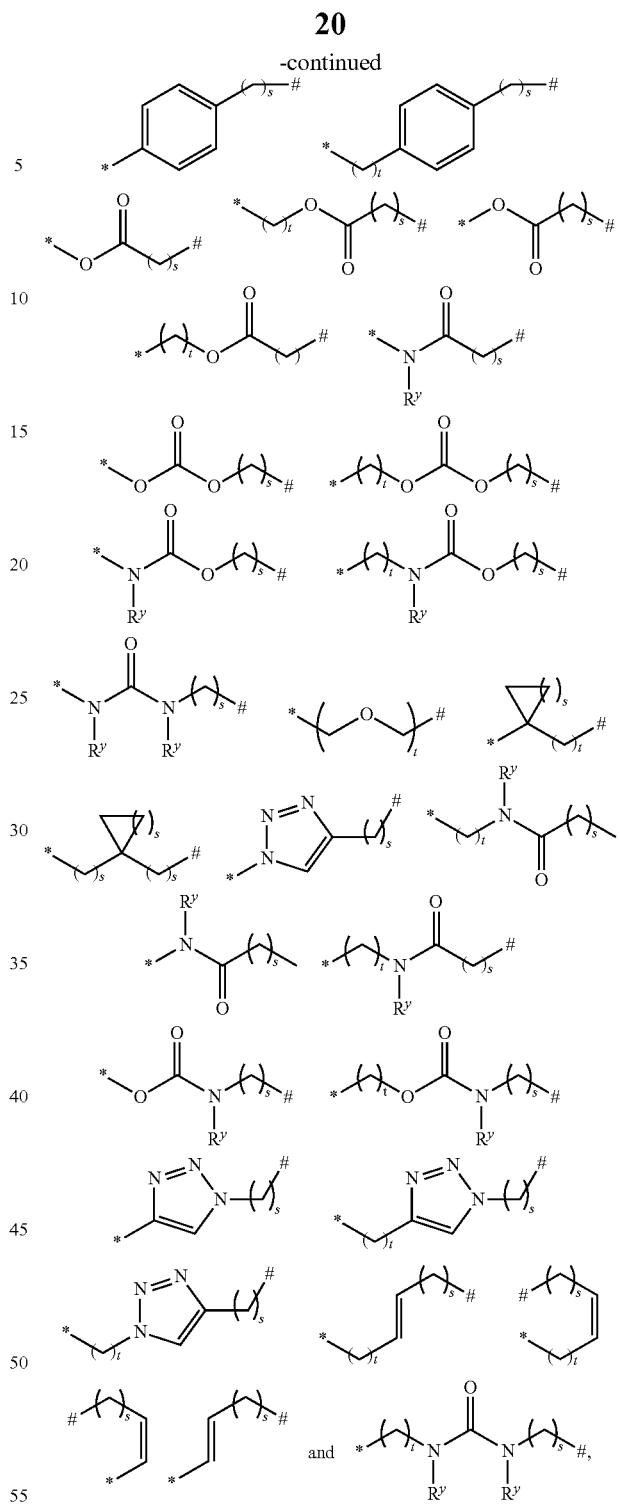

where s = 0-6 and t = 1-4 where * represents the site of attachment to the salen ligand, each # represents a site of attachment guanidinium group, and $R^y$ is —H, or an optionally substituted radical selected from the group consisting of $C_{1-6}$ aliphatic, 3- to 7-membered heterocyclic, phenyl, and 8- to 10-membered aryl. In certain embodiments, $R^y$ is other than —H.

In some embodiments, -L- is selected from the group consisting of:

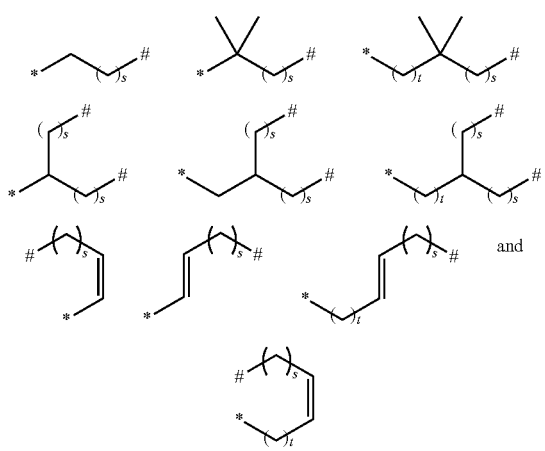

wherein s, t, *, and # are each as defined above.

In certain embodiments, —CG is selected from the group consisting of:

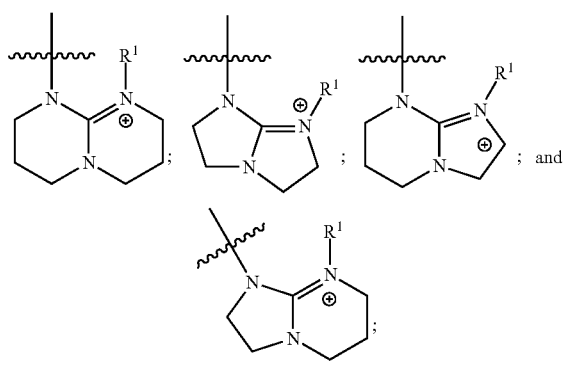

wherein $R^1$ is as defined above and described in classes and subclasses herein. In some embodiments, $R^1$ is methyl and —CG is selected from the group consisting of:

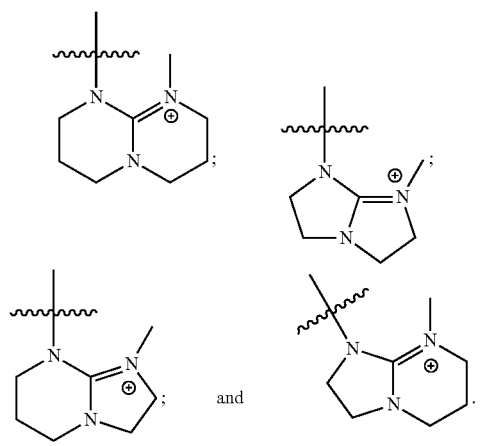

In certain embodiments, the ligand portion of provided metallosalenate complexes contains a substructure selected from the group consisting of:

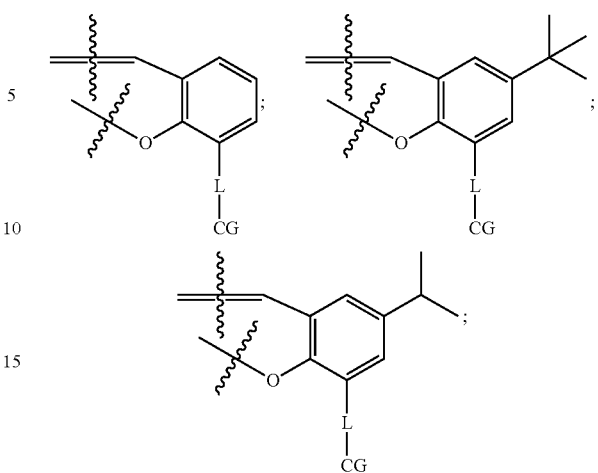

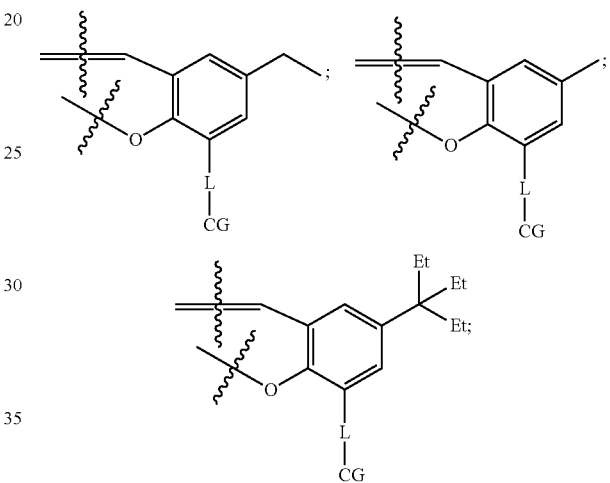

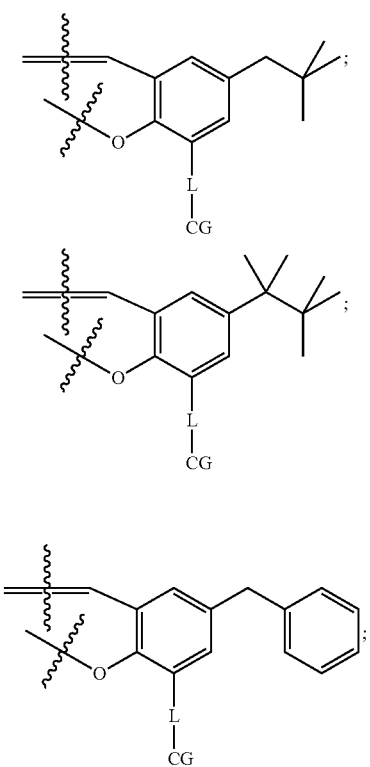

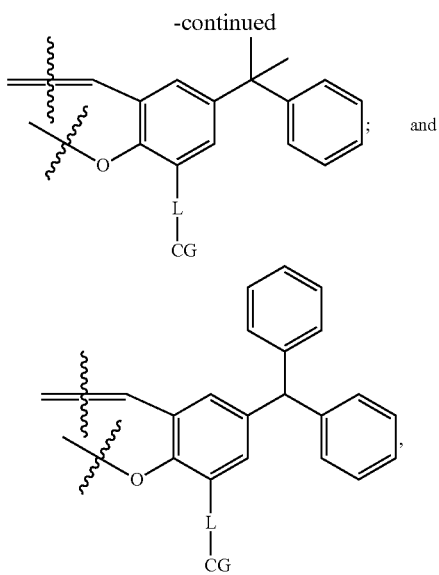

wherein -L-CG is as defined above and described in classes and subclasses herein.

In some embodiments, $R^1$ is R, wherein R is an optionally substituted moiety selected from the group consisting of $C_{1-20}$ aliphatic; $C_{1-20}$ heteroaliphatic; 3- to 8-membered saturated or partially unsaturated monocyclic carbocycle; a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring.

In some embodiments, $R^1$ is an optionally substituted moiety selected from the group consisting of $C_{1-20}$ aliphatic, $C_{1-20}$ heteroaliphatic, 3- to 7-membered heterocyclic, 3- to 7-membered carbocyclic, 6- to 10-membered aryl, and 5- to 12-membered heteroaryl. In some embodiments, $R^1$ is optionally substituted $C_{1-20}$ aliphatic. In some embodiments, $R^1$ is optionally substituted $C_{1-2}$ aliphatic. In some embodiments, $R^1$ is optionally substituted $C_{1-8}$ aliphatic. In some embodiments, $R^1$ is optionally substituted $C_{1-6}$ aliphatic. In some embodiments, $R^1$ is optionally substituted $C_{1-6}$ alkyl. In some embodiments, $R^1$ is selected from the group consisting of methyl, ethyl, n-propyl, isopropyl, n-butyl, sec-butyl, t-butyl, n-pentyl, isopentyl, neopentyl, n-hexyl, isohexyl, and neohexyl. In some embodiments, $R^1$ is methyl.

In certain embodiments, $R^1$ is $C_{1-20}$ aliphatic substituted with one or more fluoro groups. In some embodiments, $R^1$ is a perfluoro $C_{1-20}$ aliphatic group. In some embodiments, $R^1$ is a perfluoro $C_{1-20}$ alkyl group. In some embodiments, $R^1$ is $-C_nF_{(2n+1)}$, wherein n is from 1 to 40.

In some embodiments, $R^1$ is $-S(O)R$, $-S(O)_2R$, $-CO_2R$, $-C(O)R$, $-C(O)NR_2$, or $-C(O)SR$.

In some embodiments, k is 0. In some embodiments, k is 1. In some embodiments, k is 2.

In some embodiments, X and Y are independently a suitable counterion. Suitable counterions for such metal complexes are known in the art and refer to an anion or cation suitable to balance the charge. In some embodiments, a suitable counterion is a anion. In some embodiments, a suitable anion is selected from the group consisting of halide, a complex inorganic ion (e.g., perchlorate), borates, sulfonates, sulfates, phosphates, phenolates, carbonates, and carboxylates. In some embodiments, X and Y are independently halide, hydroxide, carboxylate, sulfate, phosphate, $-OR^x$, $-O(C=O)R^x$, $-O(C=O)OR^x$, $-O(C=O)N(R^x)_2$, $-NC$, $-CN$, $-NO_3$, $-N_3$, $-O(SO_2)R^x$ and $-OP(R^x)_3$, wherein each $R^x$ is, independently, selected from hydrogen, optionally substituted aliphatic, optionally substituted heteroaliphatic, optionally substituted aryl and optionally substituted heteroaryl.

It will be appreciate that in some cases, a metallosalenate complex initially comprises both a X and Y counterion, but the Y counterion is later displaced by a bidentate X counterion or a second monodentate X ligand, thereby maintaining the proper charge balance on the metallosalenate complex.

In some embodiments, k is 2 and X comprises two monodentate moieties. In some embodiments, k is 2 and X comprises a single bidentate moiety. In some embodiments, k is 2, Y is absent and X comprises a single bidentate moiety. In some embodiments, Y is absent. In some embodiments, X is carbonate.

In some embodiments, X and Y are taken together and comprise a dianion. In some embodiments, X and Y together form a diacid. In some embodiments, X and Y together form a dicarboxylic acid.

In some embodiments, Y is selected from the group consisting of halide, hydroxide, carboxylate, sulfate, phosphate, nitrate, alkyl sulfonate, and aryl sulfonate.

In some embodiments, X and Y are independently hydrogen phosphate, sulfate, a halide or carbonate. In some embodiments, X is carbonate. In some embodiments, Y is chloro, bromo, or iodo. In some embodiments, Y is chloro.

In some embodiments, M is cobalt, -L- is a bivalent $C_{1-6}$ hydrocarbon chain, $-CG$ is selected from the group consisting of:

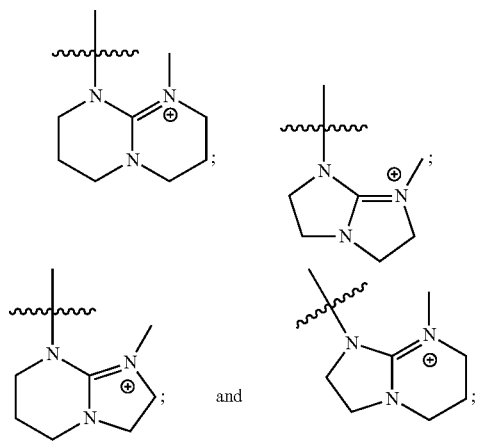

$R^1$ is methyl, X is carbonate, and k is 2.

In some embodiments of compounds of formula III-a:
M is a metal atom;
$R^1$ is $-S(O)R$, $-S(O)_2R$, $-CO_2R$, $-C(O)R$, $-C(O)NR_2$, $-C(O)SR$, a polymer, or an optionally substituted moiety selected from the group consisting of $C_{1-20}$ aliphatic, $C_{1-20}$ heteroaliphatic, 3- to 7-membered heterocyclic, 3- to 7-membered carbocyclic, 6- to 10-membered aryl, and 5- to 12-membered heteroaryl;

each R is independently an optionally substituted moiety selected from the group consisting of $C_{1-20}$ aliphatic, $C_{1-20}$ heteroaliphatic, 3- to 7-membered heterocyclic, 3- to 7-membered carbocyclic, 6- to 10-membered aryl, and 5- to 12-membered heteroaryl k is from 0-2; and X and Y are independently a suitable counterion, wherein when k is 2, X comprises two monodentate moieties or a single bidentate moiety; or X and Y are taken together to comprise a suitable dianion.

In certain embodiments, a provided metallosalenate complex has the structure:

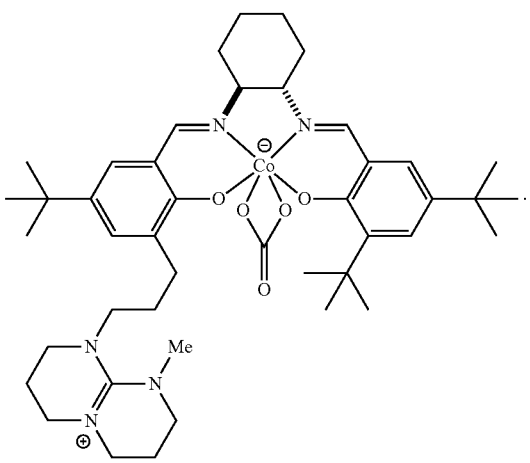

As discussed above, it is possible for a free secondary amine group of a guanidinium group to form a covalent bond with a polymer chain. Thus, in cases where such secondary amine groups are left as free amines, such polymer-bound metallosalenate complexes may form. Therefore, the present invention provides such metallosalenate complexes that are polymer bound. In certain embodiments, the present invention provides a metallosalenate complex comprising a cationic bicyclic guanidinium group, wherein the cationic bicyclic guanidinium group has no free amines, and wherein the guanidinium group is covalently bonded to a polymer. In some embodiments, the $R^1$ group of a —CG group is or comprises a polymer. In some embodiments, a suitable linker may be used to link $R^1$ to a polymer backbone. Suitable polymers include polyether, polyolefins, and polystyrenes. In some embodiments, a polymer is soluble (in solution phase) in a suitable solvent. In some embodiments, a polymer is in solid phase. In certain embodiments, a cationic bicyclic guanidinium group is selected from the group consisting of:

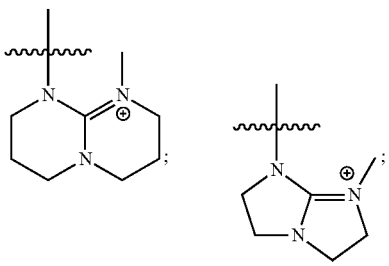

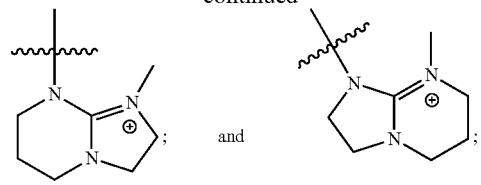

wherein $R^1$ is a polymer. In certain embodiments, $R^1$ is a polycarbonate.

Provided metal complexes allow for the polymerization of epoxides and carbon dioxide while avoiding or lessening covalent binding of the metal complex to the polymer. In some embodiments, the present invention provides a method comprising the step of contacting an epoxide and carbon dioxide with a provided metallosalenate complex to form a polycarbonate polymer composition, wherein the polycarbonate polymer composition is substantially free of covalently-bound metallosalenate complex or any guanidine-containing portion thereof.

In certain embodiments, the present invention provides a method comprising the steps of:

i. contacting an epoxide and carbon dioxide with a metallosalenate complex to form a polycarbonate polymer composition; and ii. performing chromatography to obtain isolated polycarbonate polymer composition.

In some embodiments, an isolated polycarbonate polymer composition is pure. In some embodiments, an isolated polycarbonate polymer composition is 80%, 85%, 90%, 91%, 92%, 93%, 94%, 95%, 96%, 97%, 98%, or 99% pure. In some embodiments, an isolated polycarbonate polymer composition is substantially free of the metallosalenate complex or any guanidine-containing portion thereof.

In some embodiments, the present invention provides a method comprising the steps of:

i. contacting an epoxide and carbon dioxide with a metallosalenate complex to form a polycarbonate polymer composition; and ii. performing chromatography to obtain substantially isolated, intact metallosalenate complex.

EXEMPLIFICATION

Example 1

This example describes the synthesis of catalyst A (a compound of formula III where $R^1$=Methyl).

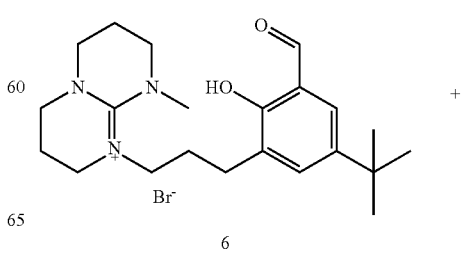

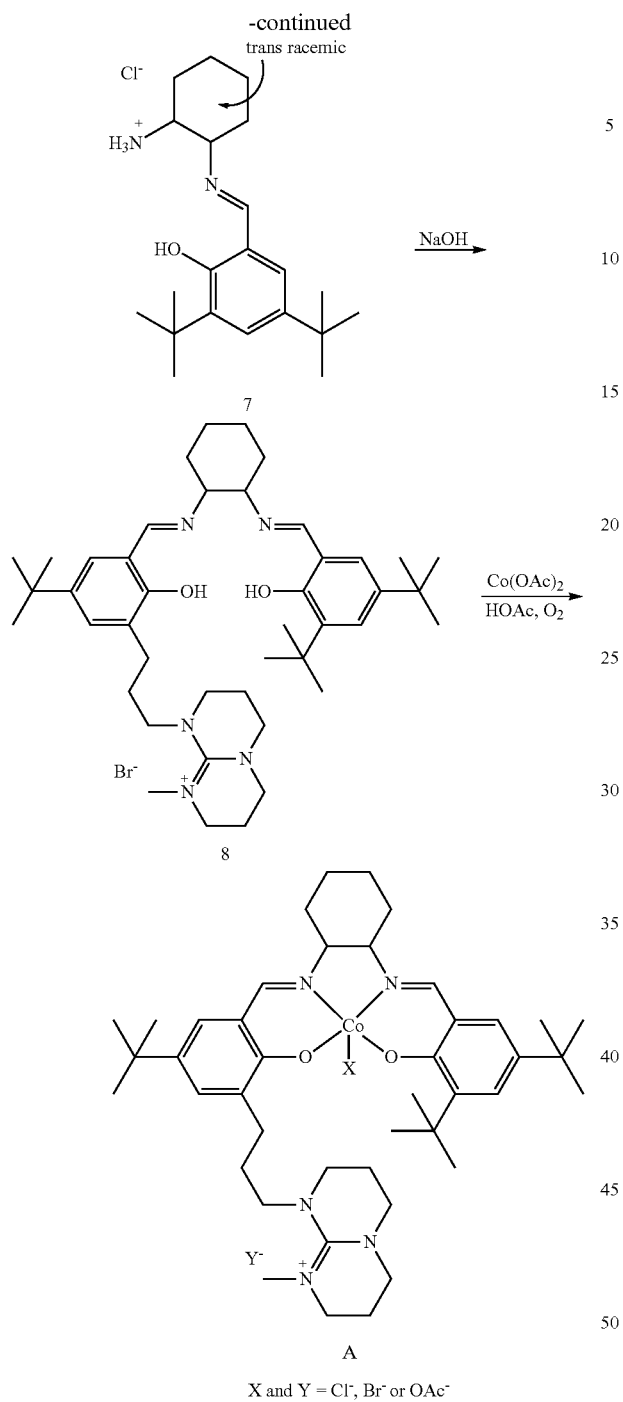

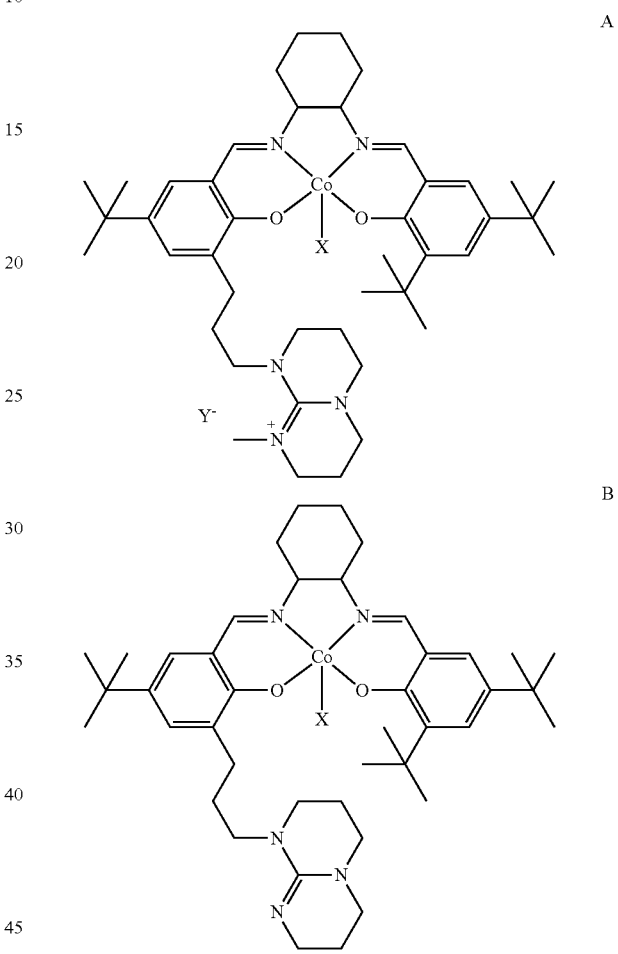

X and Y = Cl⁻, Br⁻ or OAc⁻

Figure 2:
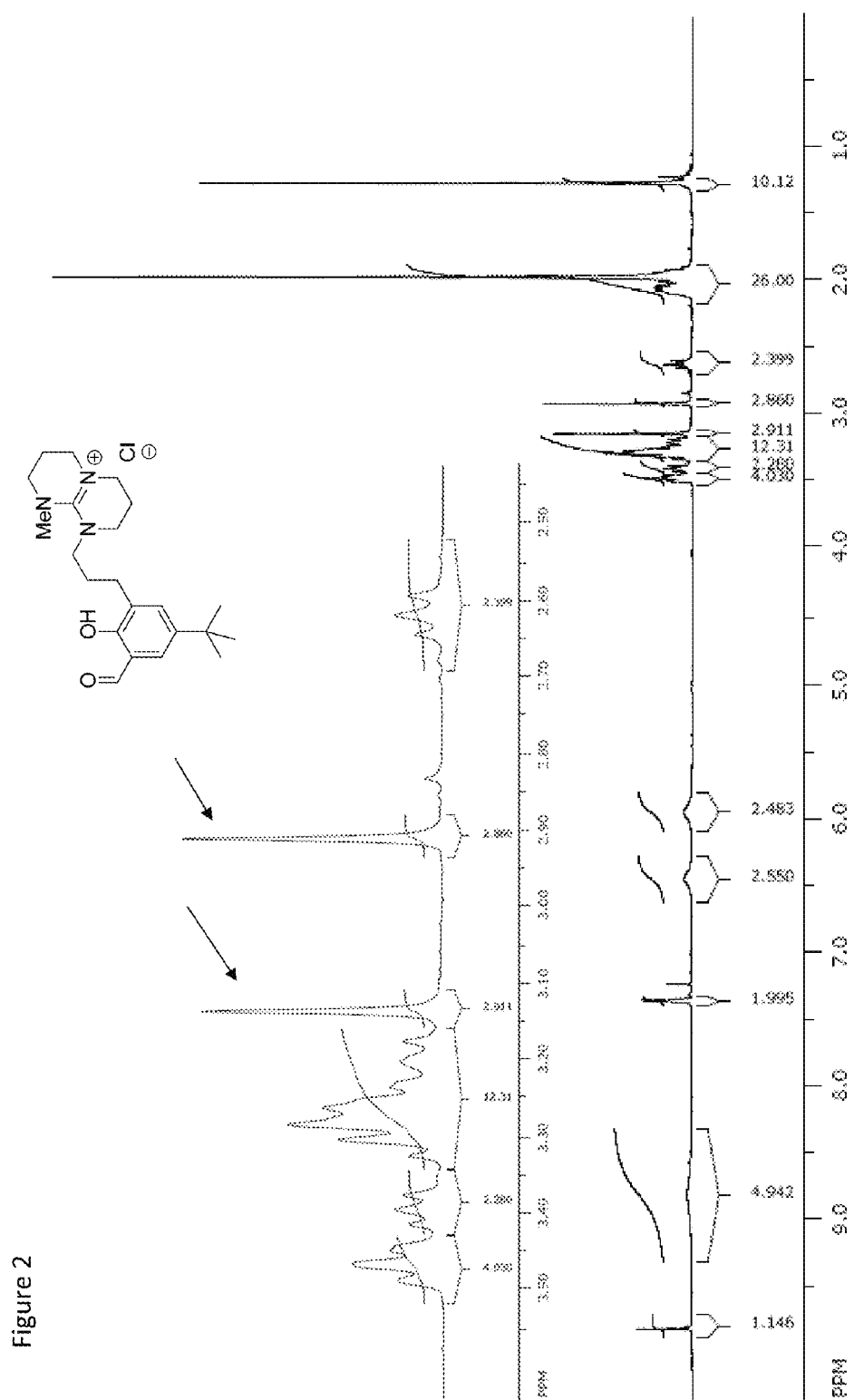
FIG. 2 is a $^1$H-NMR spectrum of intermediate compound 6.

A 10 wt % ethanolic solution of aldehyde 6 (6 is made according to Example 9 of WO 2012/040454) is contacted with an equimolar amount of the known ammonium salt 7 (described in *Chemical Communications* (2010), 46(17), 2935-2937) in the presence of NaOH to provide ligand 8. The ligand is treated with cobalt(II) acetate to afford the cobalt(II) complex and liberate two equivalents of acetic acid. This complex is oxidized in the presence of air to provide the desired catalyst. The ¹H-NMR spectrum of this catalyst after conversion to its carbonate salt is shown in FIG. 1. While not wishing to be bound by any particular theory, it is believed that the two methyl groups depicted in the ¹H-NMR spectrum of Catalyst A represent isomers of the compound (see FIG. 1, arrows). Such isomer forms may also be seen in the ¹H-NMR of compound 6 (see FIG. 2, arrows).

Example 2

This example compares the post-polymerization processability of crude polymer compositions produced with catalyst (B) and with the catalyst described in Example 1 (A).

i) Polymerization Procedure.

Two 300 mL Stainless steel pressure reactors are dried in vacuo, using a hot plate (120° C.) and cooled to rt. Each reactor is charged with catalyst, one with catalyst A, and the other with B (each 30 mg, 3.7×10⁻⁵ mol). The reactors are evacuated for 15 min, then backfilled with nitrogen, this procedure is repeated twice more. While under the positive flow of nitrogen, propylene oxide (50 mL, 0.71 mol) and dipropylene glycol (2.2 g, 0.015 mol) are charged to each reaction vessel. The vessels are pressurized to 300 psi with carbon dioxide and heated to 50° C.

Figure 3:
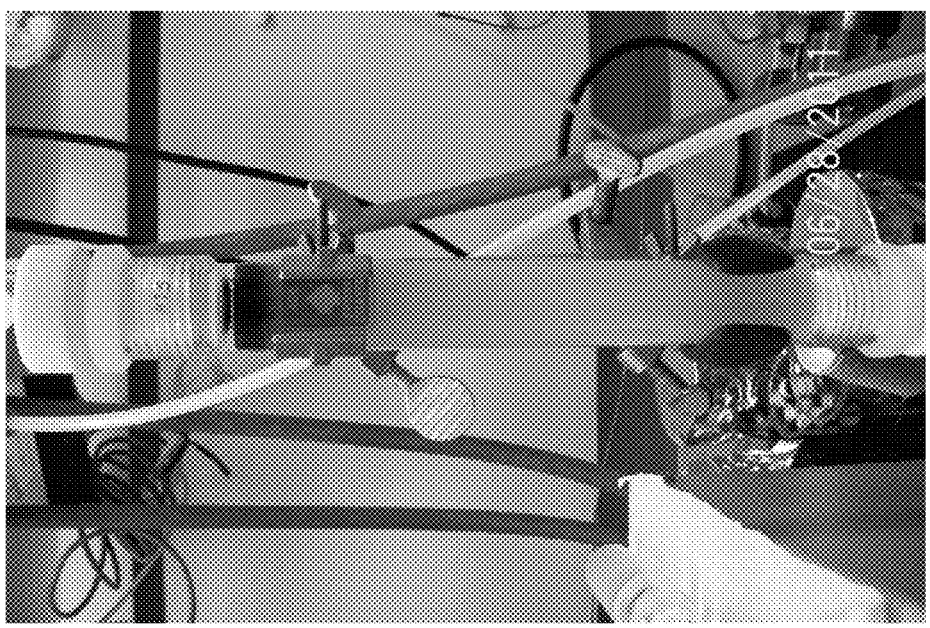
FIGS. 3 and 4 are photographs of silica gel chromatography polymer dope from catalyst A pumped onto a silica gel column and eluted, as described in Example 2.
Figure 4:
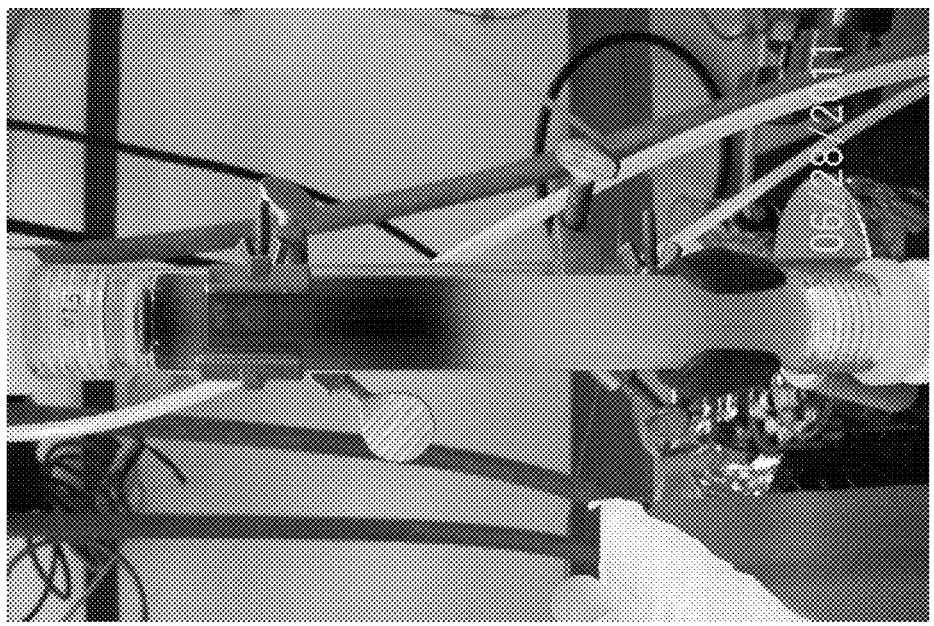
Figure 5:
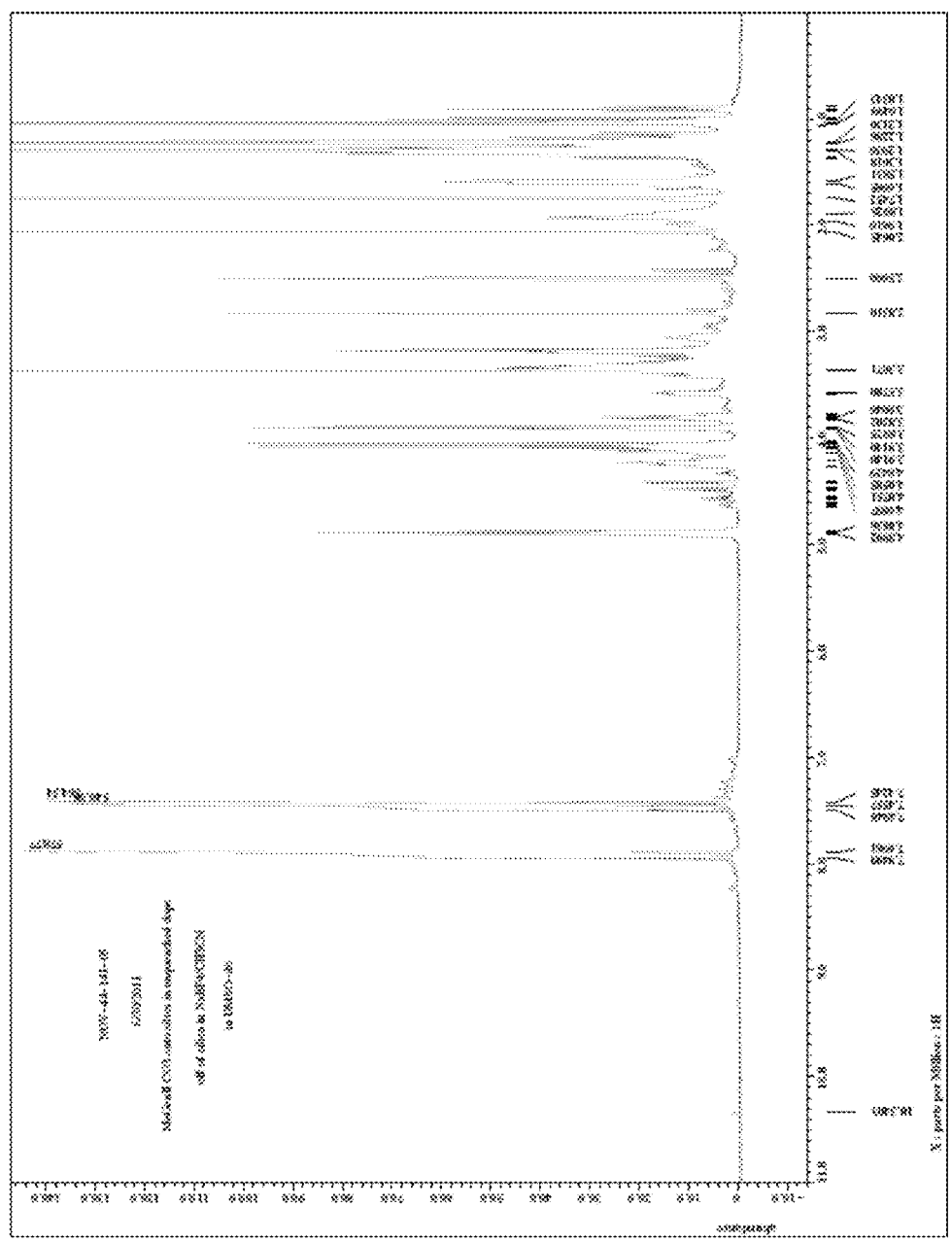
FIG. 5 is a $^1$H-NMR spectrum of catalyst A (bis-$BF_4^-$ salt) recovered from silica gel chromatography.

After stirring at this temperature for 8 h, the reaction vessels are cooled to ambient temperature and vented, and the contents are diluted by addition of acetonitrile (100 mL) to provide dark brown polymer solutions containing approximately 30 wt % of PPC (Mn between 2900 and 3100 g/mol).

ii) Catalyst Removal:

Each polymer solution is pumped at a rate of 3 ml/minute onto a separate 15 mm×150 mm column loaded with 12 g of silica gel saturated with acetonitrile. Once the entirety of each polymer solution has been pumped onto each column, 50 mL additional acetonitrile followed by 100 mL of 0.1M NaBF$_4$ in acetonitrile is pumped through at a rate of 1 mL/minute. The effluent from the initial loading and the additional acetonitrile rinse are collected in a flask, while the eluent from the NaBF$_4$ treatment is collected in 20 mL fractions.

iii) Results: when the polymer dope from catalyst A is pumped onto the silica gel column, a dark band of catalyst is retained at the top of the column (see FIG. 3) and polymer solution exiting the column is clear and nearly colorless. When the NaBF$_4$ solution is pumped through this column, the dark band elutes from the silica gel allowing isolation of a 20 mL fraction of dark brown solution (see FIG. 4). Analysis of this fraction by LCMS and NMR shows it to contain the bis-BF$_4^-$ salt of catalyst A. See FIG. 5. Approximately 30 mg of catalyst is recovered.

Figure 6:
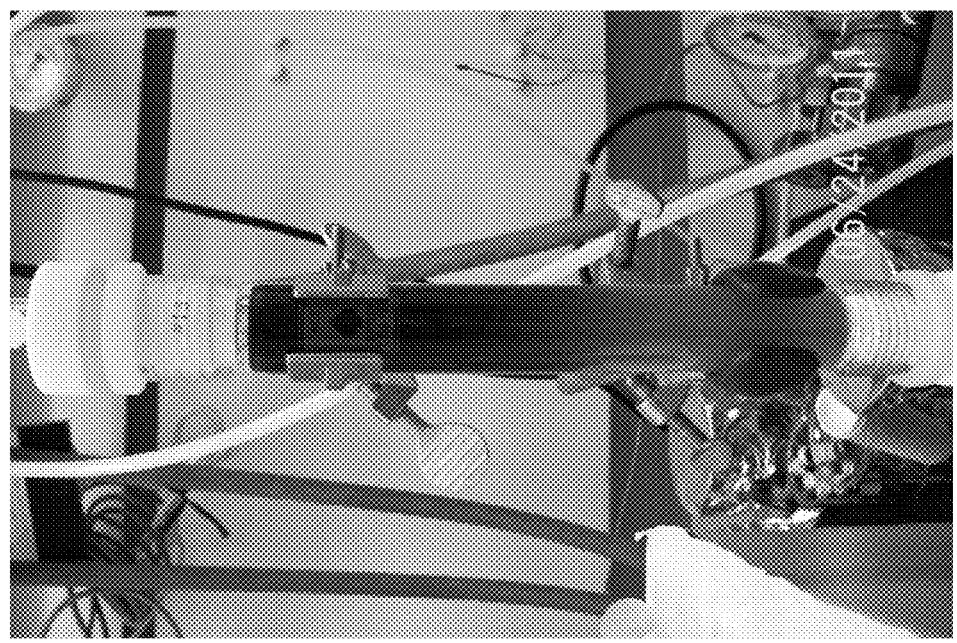
FIGS. 6 and 7 are photographs of silica gel chromatography polymer dope from catalyst B pumped onto a silica gel column and eluted, as described in Example 2.
Figure 7:
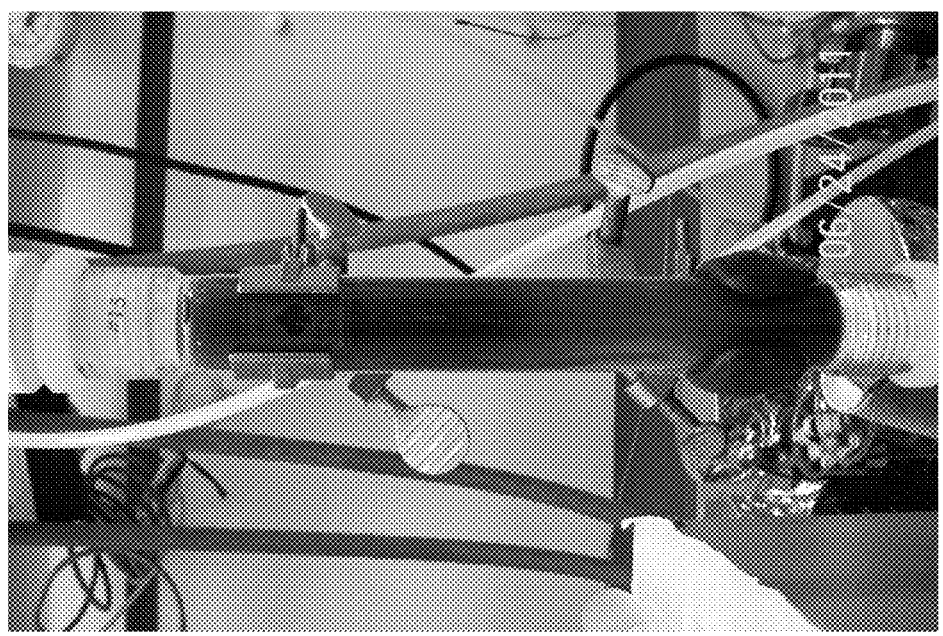

When polymer dope from Catalyst B is pumped onto the silica gel column, the entire column is colored dark brown and the polymer solution exiting the column is also colored (see FIG. 6). Subsequent elution with NaBF$_4$ solution does not elute an identifiable fraction enriched in catalyst (see FIG. 7). NMR and LCMS analyses reveal the catalyst residues recovered from this procedure contain catalyst B covalently bound to poly(propylene carbonate) chains.

Example 3

This example describes the synthesis of additional catalysts of the present invention having alternate substitution patterns on the aryl rings of the salcy ligands. Compounds 3a through 3n are synthesized according to conditions of Example 1, except ammonium salts with alternate substitution patterns on the aryl ring are employed in place of the 2,4-di-tbutyl analog 7 used in Example 1. The required ammonium salts are obtained by condensing racemic trans 1,2 cyclohexanediamine monohydrochloride with salicaldehyde analogs having the desired substituents at the 2- and/or 4-positions. In each example, the catalyst is isolated as its carbonate salt, (i.e. X and Y are taken together to be CO$_3^{2-}$).

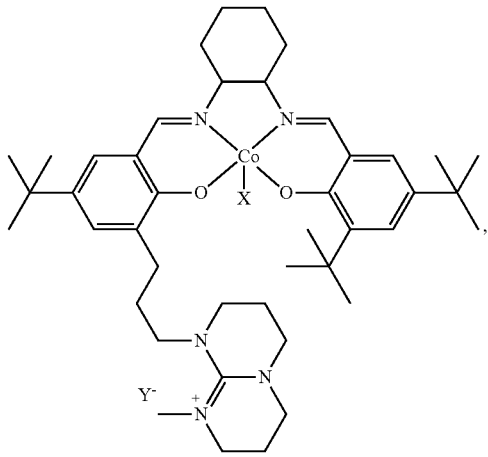

3b

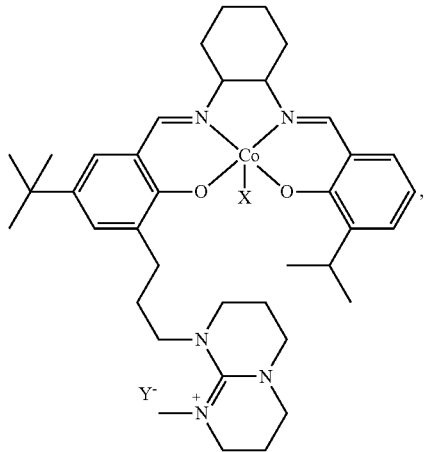

3c

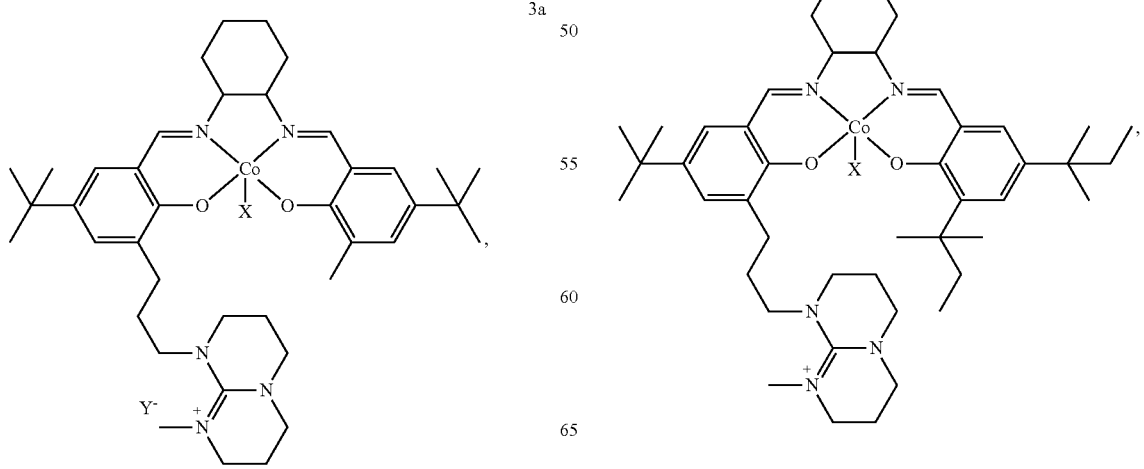

3a

3d

31
-continued
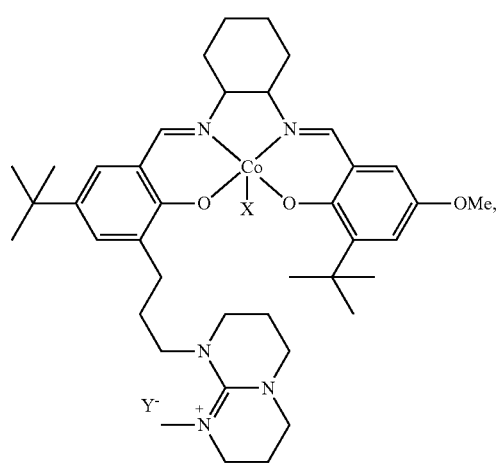
3e
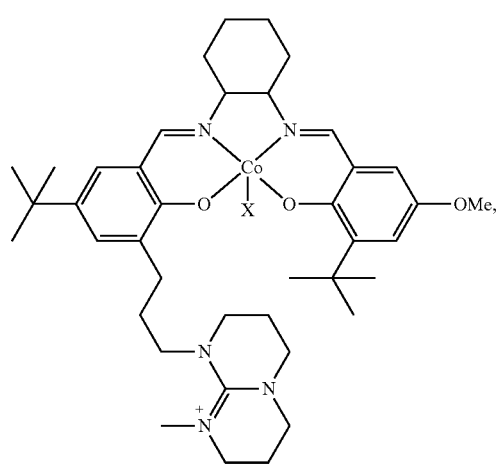
3f
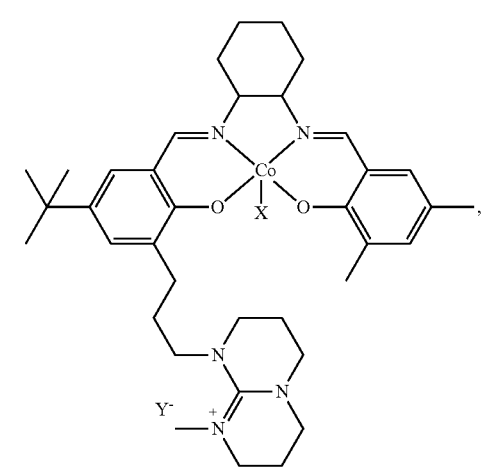
3g
32
-continued
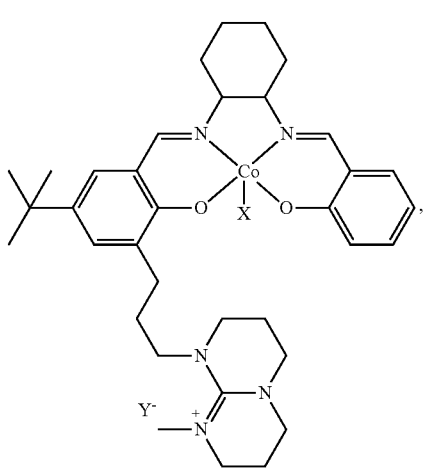
3h
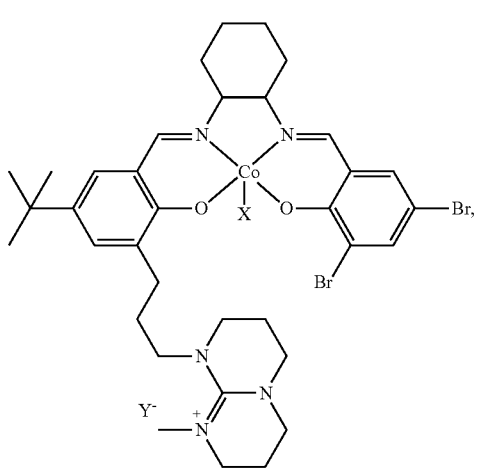
3i
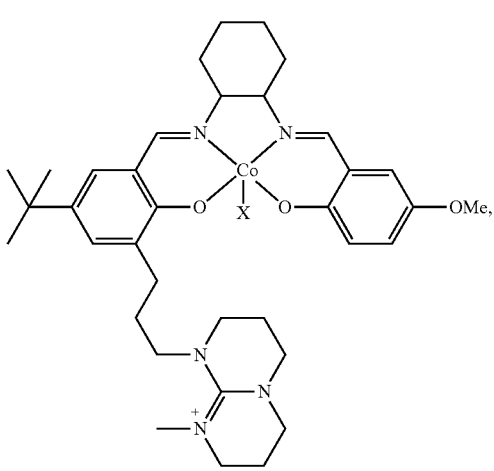
3j 33
-continued

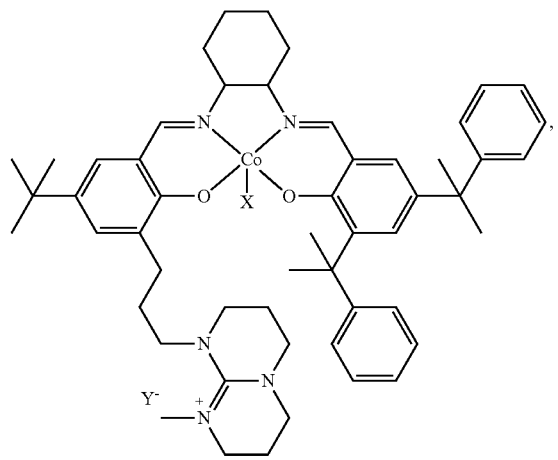

3k

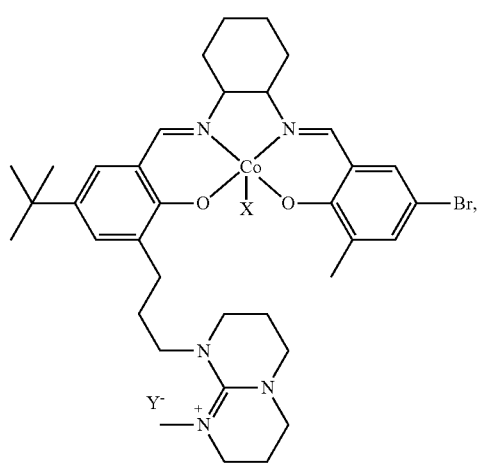

3l

3m

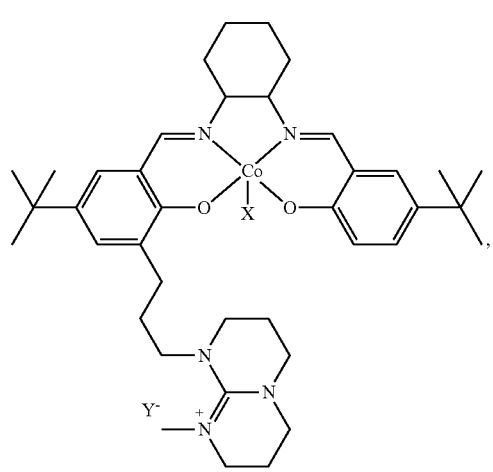

34
-continued

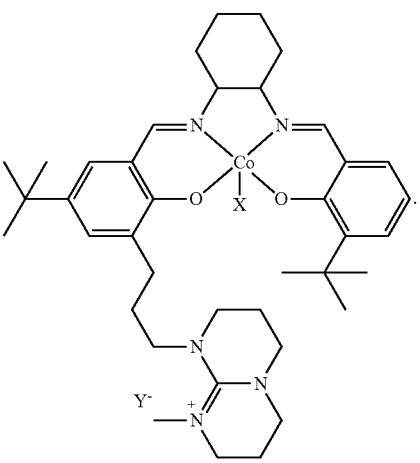

3n

Example 4

This example describes the synthesis of catalysts of the present invention having alternate bridging groups between the imine nitrogen atoms of the salen ligands. Catalyst 4a is produced according to the method of Example 1, except the required ligand is made by sequential addition of 2,4-di-tert butyl salicylaldehyde and aldehyde 6 to isobutylene diamine in the presence of 3-angstrom molecular sieves.

Catalysts 4b and 4c are produced according to the method of Example 1, by condensing aldehyde 6 with appropriate hydrochloride salts analogous to the 1,2 cyclohexane diamine-derived salt 7 used in Example 1. The required hydrochloride salts are produced in a separate step by sequential addition of one equivalent of HCl, and one equivalent of 2,4-di-tert butyl salicylaldehyde to ethylene diamine (4b) or 1,3 diaminopropane (4c).

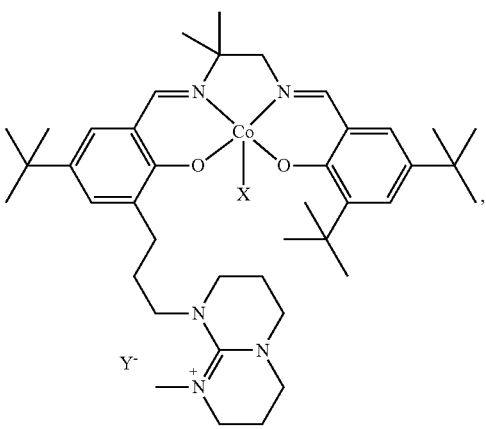

4a

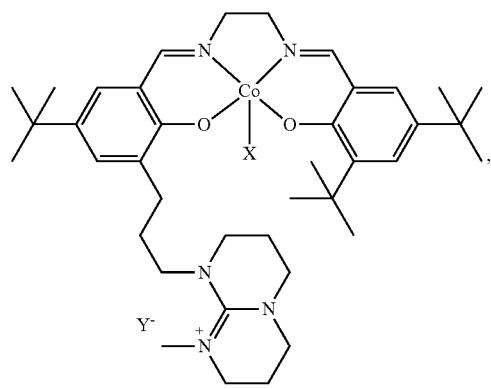
4b
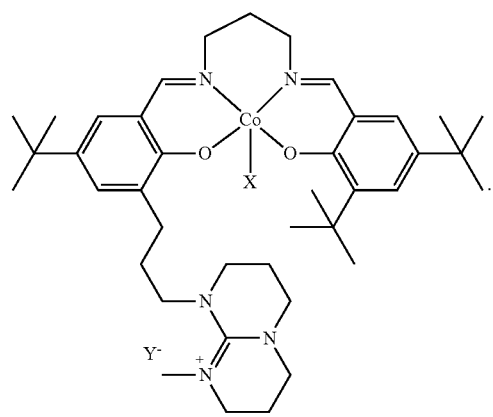
4c
Example 5
An alternative synthesis of Catalyst A is depicted in the scheme below.
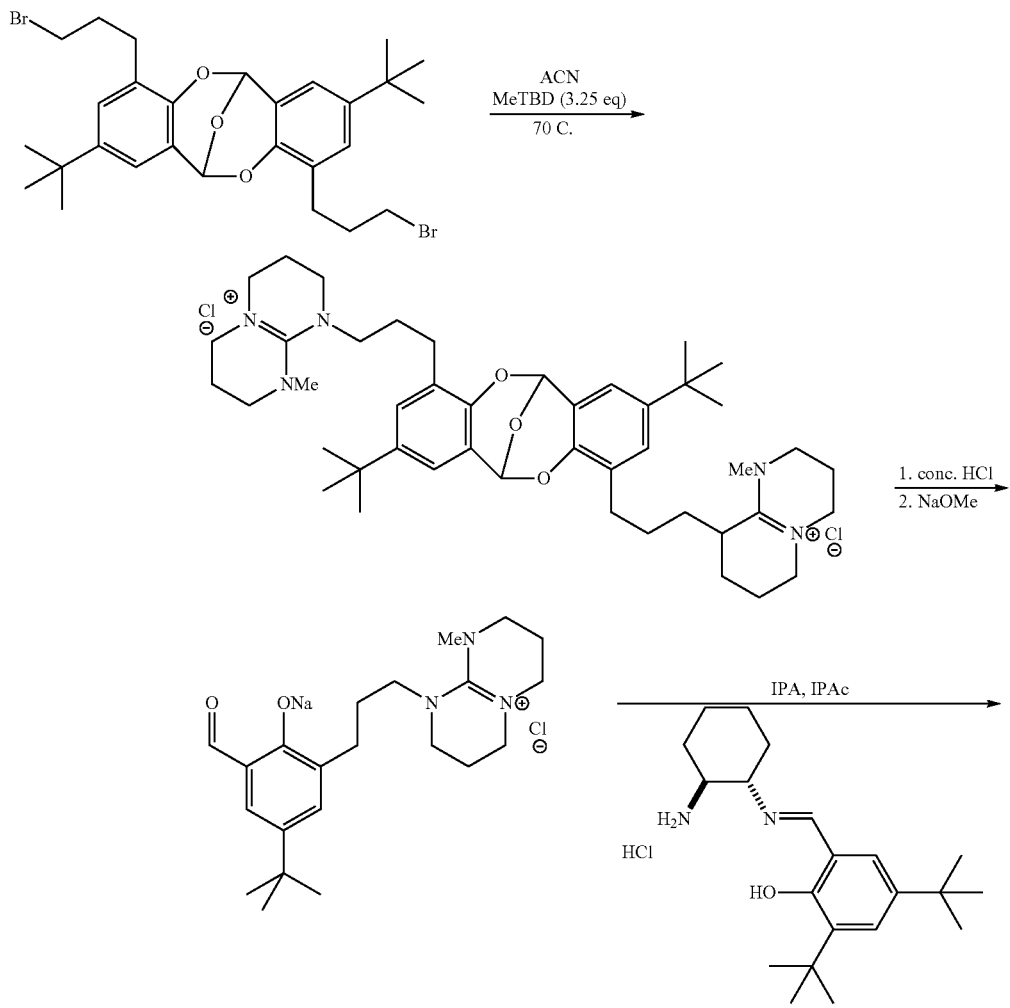

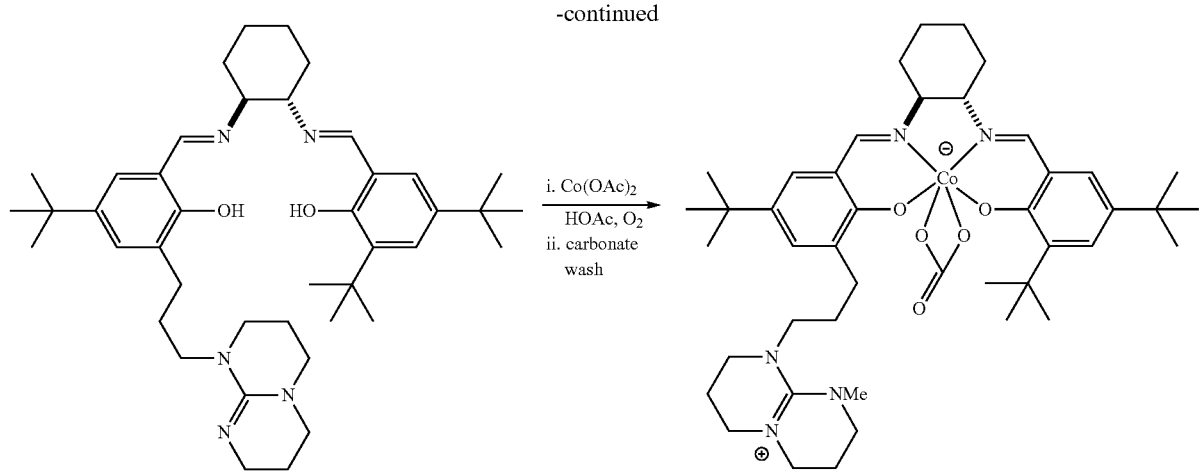

OTHER EMBODIMENTS

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A metallosalenate complex comprising a cationic bicyclic guanidinium group, wherein the cationic bicyclic guanidinium group has no free amines.

2. The metallosalenate complex of claim 1, wherein the metallosalenate complex is of formula I:

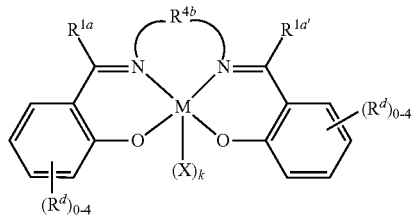

wherein, $R^{1a}$ and $R^{1a'}$ independently a hydrogen or an optionally substituted radical selected from the group consisting of $C_{1-12}$ aliphatic; $C_{1-12}$ heteroaliphatic; phenyl; a 3- to 8-membered saturated or partially unsaturated monocyclic carbocycle, a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur;

each $R^d$ is independently a -L-CG group, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of $C_{1-20}$ aliphatic; $C_{1-20}$ heteroaliphatic; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more $R^d$ groups may be taken together with intervening atoms to form one or more optionally substituted rings optionally containing one or more heteroatoms, wherein at least one occurrence of $R^d$ is a -L-CG group;

each L is independently a covalent bond or an optionally substituted, saturated or unsaturated, straight or branched, bivalent $C_{1-12}$ hydrocarbon chain, wherein one or more methylene units of L are optionally and independently replaced by -Cy-, —CR$_2$—, —NR—, —N(R)C(O)—, —C(O)N(R)—, —N(R)SO$_2$—, —SO$_2$(R)—, —O—, —C(O)—, —OC(O)—, —OC(O)O—, —C(O)O—, —N(R)C(O)O—, —SiR$_2$—, —S—, —SO—, or —SO$_2$—;

each CG is independently a cationic bicyclic guanidinium group having no free amines;

each Cy is independently an optionally substituted bivalent ring selected from phenylene, a 3-7 membered saturated or partially unsaturated carbocyclylene, a 3-7 membered saturated or partially unsaturated monocyclic heterocyclylene having 1-2 heteroatoms independently selected from nitrogen, oxygen, or sulfur, or a 5-6 membered heteroarylene having 1-3 heteroatoms independently selected from nitrogen, oxygen;

$R^{4b}$ is selected from the group consisting of:

e)

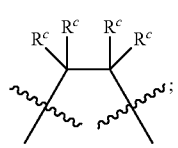

-continued f)

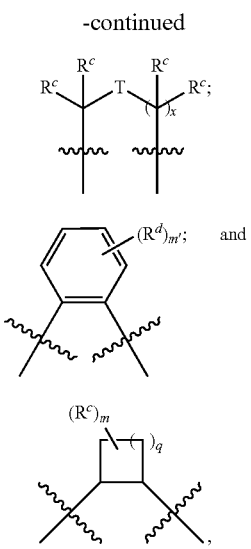

g)

h)

where
R<sup>c</sup> at each occurrence is independently hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or an optionally substituted radical selected from the group consisting of C$_{1-20}$ aliphatic; C$_{1-20}$ heteroaliphatic; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; where two or more R<sup>c</sup> groups may be taken together with the carbon atoms to which they are attached and any intervening atoms to form one or more optionally substituted rings;

R at each occurrence is independently hydrogen, an optionally substituted radical selected the group consisting of acyl; C$_{1-20}$ aliphatic; C$_{1-20}$ heteroaliphatic; carbamoyl; arylalkyl; phenyl; a 3- to 8-membered saturated or partially unsaturated monocyclic carbocycle, a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring;

T is a divalent linker selected from the group consisting of: —NR—, —N(R)C(O)—, —C(O)NR—, —O—, —C(O)—, —OC(O)—, —C(O)O—, —S—, —SO—, —SO$_2$—, —SiR$_2$—, —C(=S)—, —C(=NR)—, or —N=N—; a polyether; a C$_3$ to C$_8$ substituted or unsubstituted carbocycle; and a C$_1$ to C$_8$ substituted or unsubstituted heterocycle;

M is a metal atom;

each X is independently a suitable counterion;

k is from 0 to 2, inclusive;

m is from 0 to 6, inclusive;

m' is from 0 to 4, inclusive;

q is from 0 to 4, inclusive; and x is from 0 to 2, inclusive.

3. The metallosalenate complex of claim 2, wherein the metallosalenate complex is of formula II or II-a:

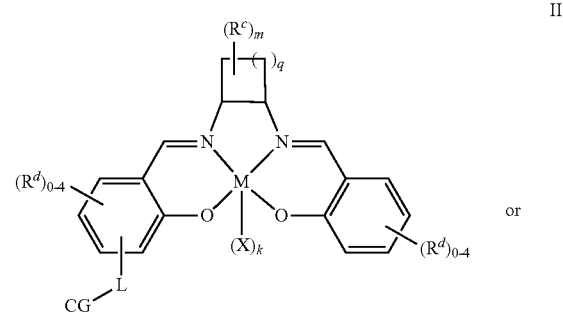

II or

II-a

4. The metallosalenate complex of claim 3, wherein the metallosalenate complex is of formula II-aa, II-bb, II-cc, II-dd, II-ee, II-ff, II-gg, or II-hh:

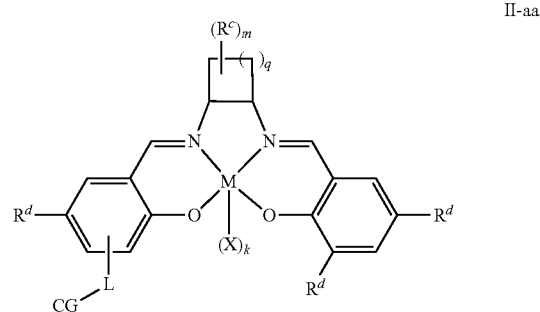

II-aa

-continued

II-bb
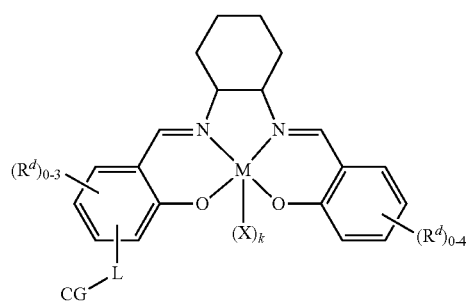

II-cc
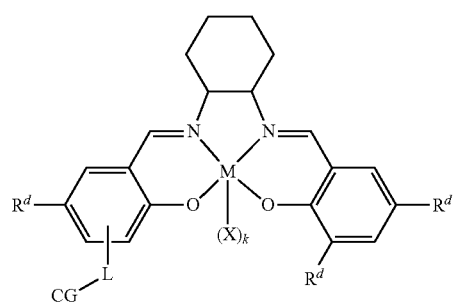

II-dd
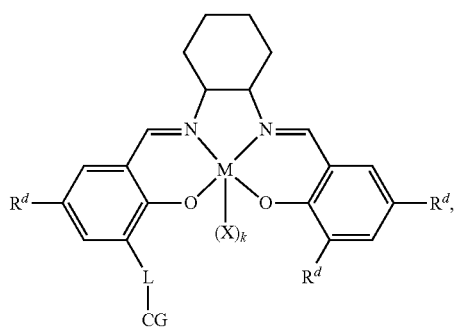

II-ee
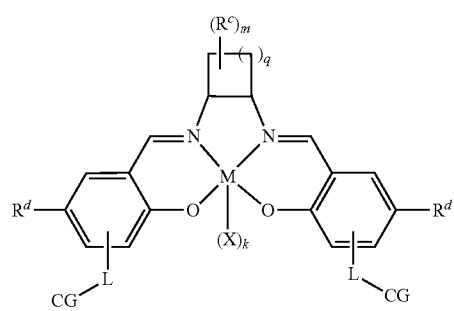

II-ff
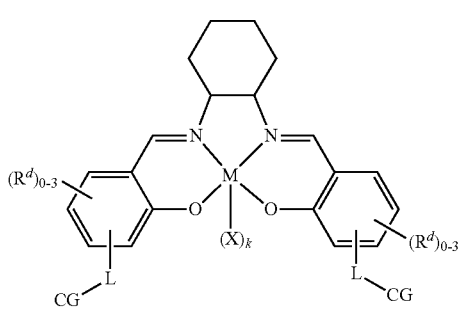

-continued

II-gg
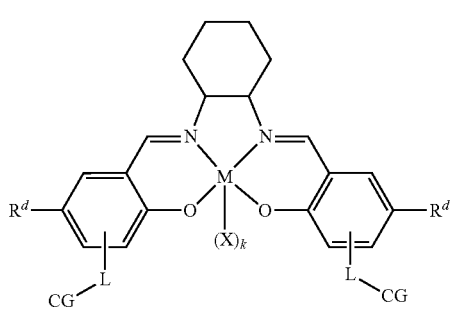

II-hh
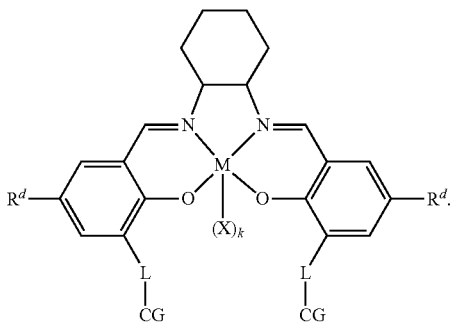

5. The metallosalenate complex of claim 1, wherein $R^{1a}$ and $R^{1a'}$ are hydrogen.

6. The metallosalenate complex of claim 2, wherein M is selected from the group consisting of Cr, Mn, V, Fe, Co, Mo, W, Ru, Al, and Ni.

7. The metallosalenate complex of claim 6, wherein one occurrence of $R^d$ is a -L-CG group, and any other $R^d$ groups are an optionally substituted $C_{1-20}$ aliphatic group or an optionally substituted phenyl group.

8. The metallosalenate complex of claim 2, wherein -L- is an optionally substituted, saturated or unsaturated, straight or branched, bivalent $C_{1-6}$ hydrocarbon chain, wherein one, two, or three methylene units of L are optionally and independently replaced by -Cy-, —$CR_2$—, —NR—, —N(R)C(O)—, —C(O)N(R)—, —N(R)SO$_2$—, —SO$_2$N(R)—, —O—, —C(O)—, —OC(O)—, —OC(O)O—, —C(O)O—, —N(R)C(O)O—, —SiR$_2$—, —S—, —SO—, or —SO$_2$—.

9. The metallosalenate complex of claim 8, wherein -L- is an optionally substituted, saturated or unsaturated, straight or branched, bivalent $C_{1-6}$ hydrocarbon chain, wherein one or two methylene units of L are optionally and independently replaced by —NR—, —O—, or —C(O)—.

10. The metallosalenate complex of claim 9, wherein -L- is —(CH$_2$)$_{1-6}$—.

11. The metallosalenate complex of claim 2, wherein -L- is selected from the group consisting of:

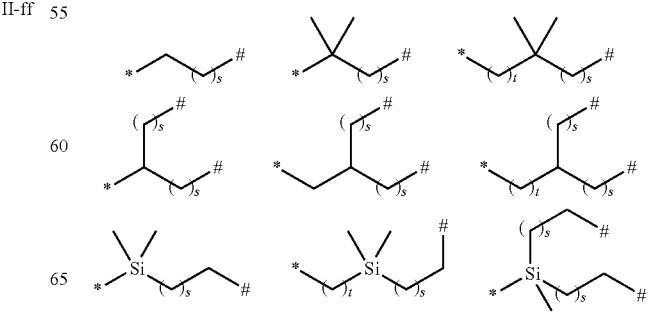

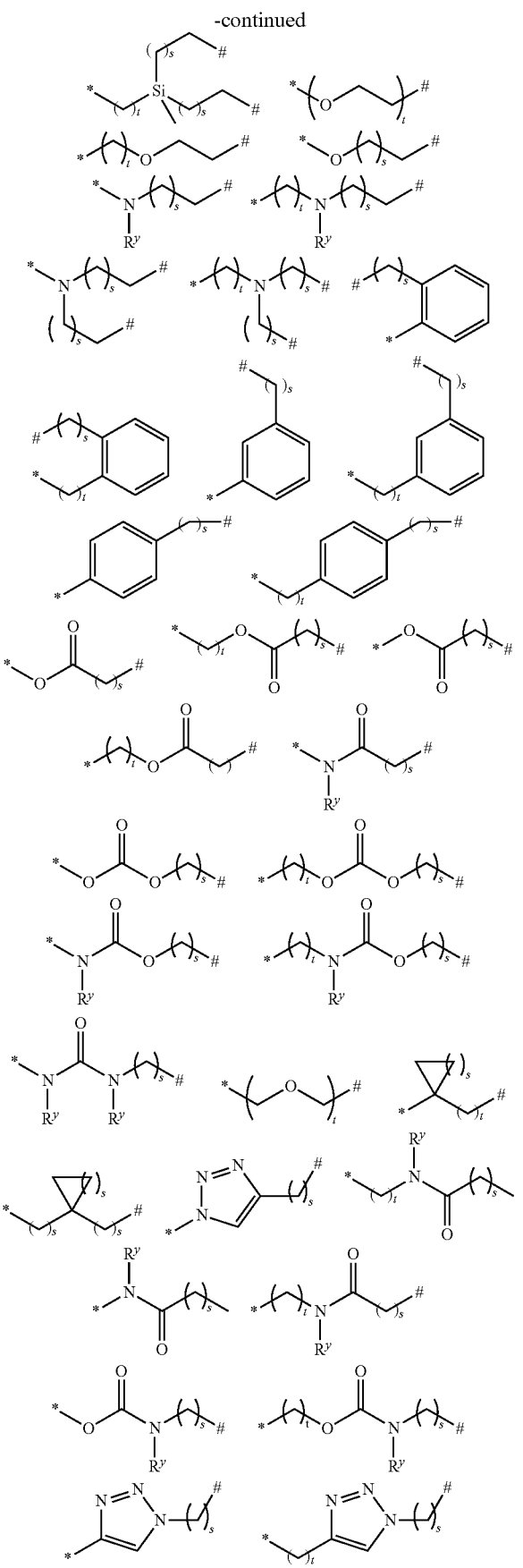

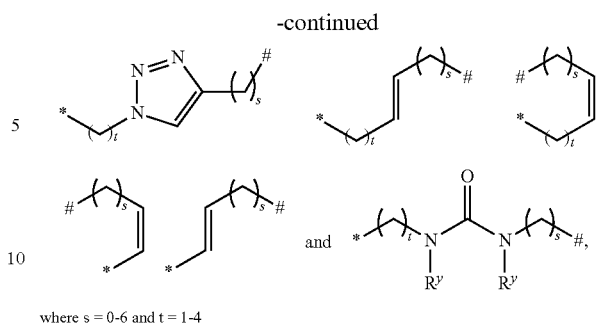

where s = 0-6 and t = 1-4 where * represents the site of attachment to the salen ligand, each # represents a site of attachment guanidinium group, and $R^y$ is —H, or an optionally substituted radical selected from the group consisting of $C_{1-6}$ aliphatic, 3- to 7-membered heterocyclic, phenyl, and 8- to 10-membered aryl.

12. The metallosalenate complex of claim 8, wherein CG is selected from the group consisting of:

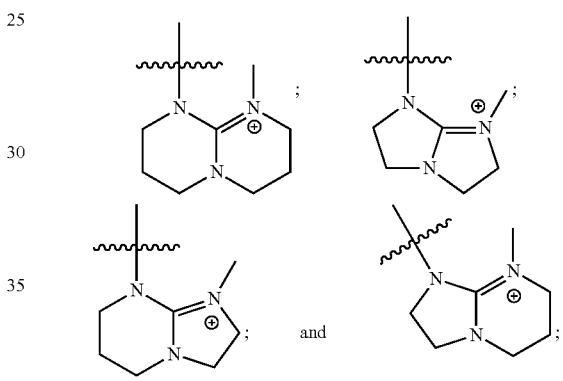

wherein:

$R^1$ is —S(O)R, —S(O)$_2$R, —CO$_2$R, —C(O)R, —C(O)NR$_2$, —C(O)SR, or R; and each R is independently an optionally substituted moiety selected from the group consisting of $C_{1-20}$ aliphatic; $C_{1-20}$ heteroaliphatic; 3- to 8-membered saturated or partially unsaturated monocyclic carbocycle; a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring.

13. The metallosalenate complex of claim 12, wherein CG is selected from the group consisting of:

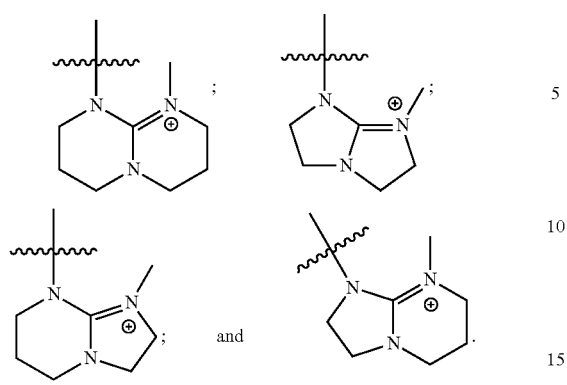
14. The metallosalenate complex of claim 2, wherein the ligand portion of the metal complex comprises a substructure selected from the group consisting of:
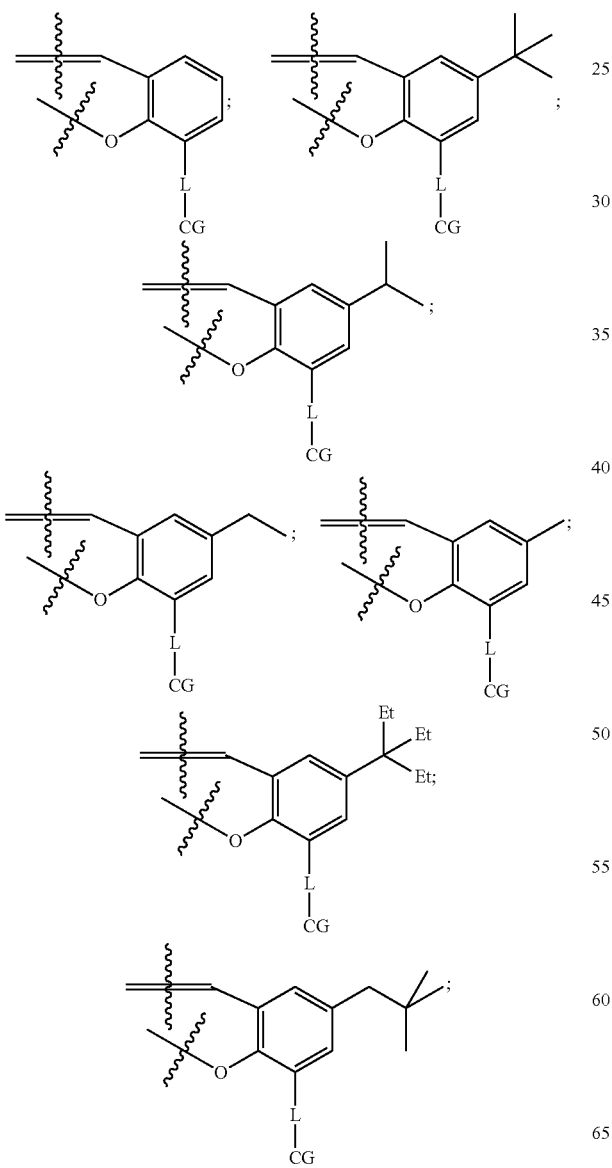
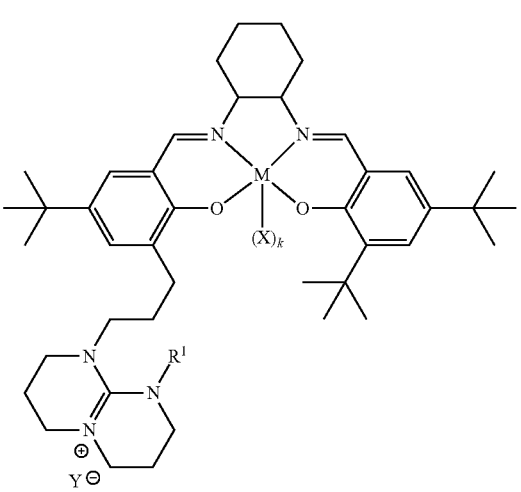
15. The metallosalenate complex of claim 2, wherein the metal complex is of formula III:
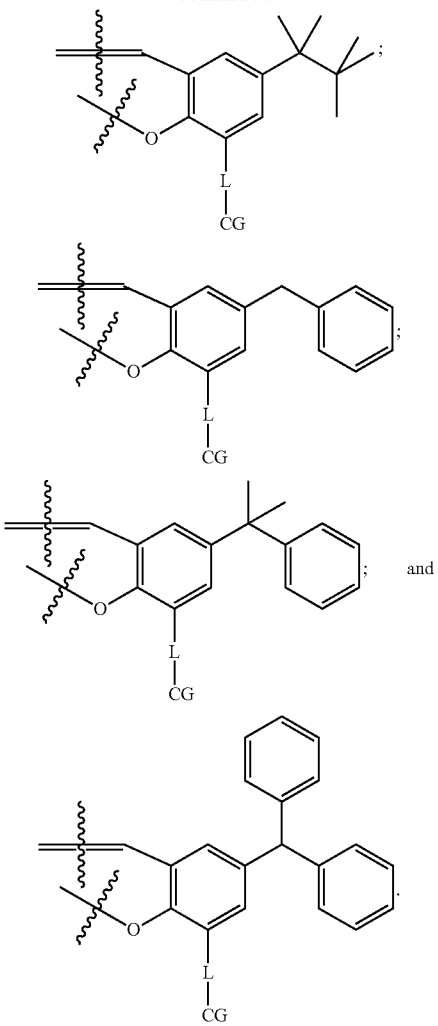

wherein:

R¹ is —S(O)R, —S(O)₂R, —CO₂R, —C(O)R, —C(O)NR₂, —C(O)SR, or R;

each R is independently an optionally substituted moiety selected from the group consisting of $C_{1-20}$ aliphatic; $C_{1-20}$ heteroaliphatic; 3- to 8-membered saturated or partially unsaturated monocyclic carbocycle; a 7- to 14-membered saturated, partially unsaturated or aromatic polycyclic carbocycle; a 5- to 6-membered monocyclic heteroaryl ring having 1-4 heteroatoms independently selected from nitrogen, oxygen, or sulfur; a 3- to 8-membered saturated or partially unsaturated heterocyclic ring having 1-3 heteroatoms independently selected from nitrogen, oxygen, or sulfur; a 6- to 12-membered polycyclic saturated or partially unsaturated heterocycle having 1-5 heteroatoms independently selected from nitrogen, oxygen, or sulfur; or an 8- to 10-membered bicyclic heteroaryl ring having 1-5 heteroatoms independently selected from nitrogen, oxygen, or sulfur; an oxygen protecting group; and a nitrogen protecting group, where two R groups on the same nitrogen atom can optionally be taken together to form an optionally substituted 3- to 7-membered ring; and each X is independently a suitable counterion; and Y, when present, is a suitable counterion;

wherein when k is 2, Y is absent and X comprises two monodentate moieties or a single bidentate moiety, or X and Y are taken together to comprise a suitable dianion.

16. The metallosalenate complex of claim 15, wherein the metal complex is of formula III-a:

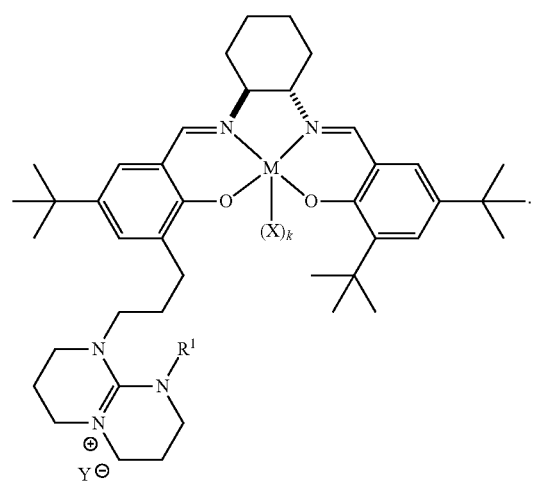

III-a

17. The metallosalenate complex of claim 15, wherein R¹ is selected from the group consisting of methyl, ethyl, n-propyl, isopropyl, n-butyl, sec-butyl, t-butyl, n-pentyl, isopentyl, neopentyl, n-hexyl, isohexyl, and neohexyl.

18. The metallosalenate complex of claim 17, wherein R¹ is methyl.

19. The metallosalenate complex of claim 15, wherein Y is selected from the group consisting of halide, hydroxide, carboxylate, sulfate, phosphate, nitrate, alkyl sulfonate, and aryl sulfonate.

20. The metallosalenate complex of claim 19, wherein Y is chloro, bromo, or iodo.

21. The metallosalenate complex of claim 20, wherein Y is chloro.

22. The metallosalenate complex of claim 2, wherein X is selected from the group consisting of —OR$^x$, —O(C=O)R$^x$, —O(C=O)OR$^x$, —O(C=O)N(R$^x$)₂, —NC, —CN, —NO₃, halogen, —N₃, —O(SO₂)R$^x$ and —OPR$^x$₃, wherein each R$^x$ is, independently, selected from hydrogen, optionally substituted aliphatic, optionally substituted heteroaliphatic, optionally substituted aryl and optionally substituted heteroaryl.

23. The metallosalenate complex of claim 2, wherein k is 1.

24. The metallosalenate complex of claim 2, wherein k is 2.

25. The metallosalenate complex of claim 24, wherein X is carbonate.

26. The metallosalenate complex of claim 15, wherein R¹ is methyl, X is carbonate, and k is 2.

27. The metallosalenate complex of claim 2, wherein M is cobalt.

28. The metallosalenate complex of claim 15 having the structure:

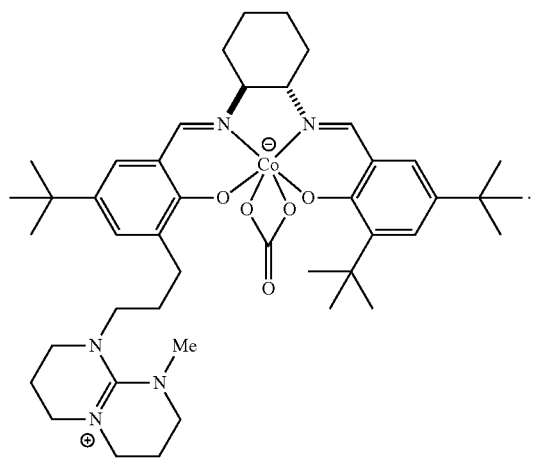

29. A metallosalenate complex comprising a cationic bicyclic guanidinium group, wherein the cationic bicyclic guanidinium group has no free amines, and wherein the guanidinium group is covalently bonded to a polymer.

30. The metallosalenate complex of claim 29, wherein cationic bicyclic guanidinium group is selected from the group consisting of:

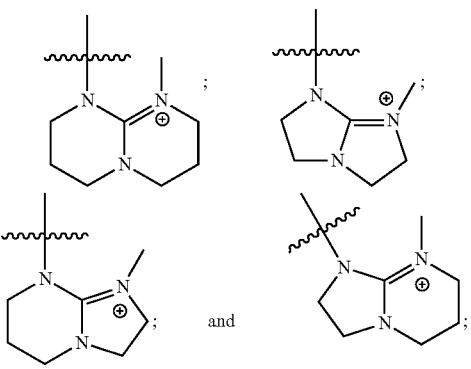

wherein R¹ is a polymer.

31. A method comprising the step of contacting an epoxide and carbon dioxide with a metallosalenate complex of claim 1 to form a polycarbonate polymer composition, wherein the polycarbonate polymer composition is substantially free of covalently-bound metal complex or any guanidine-containing portion thereof.

32. A method comprising the steps of:

i. contacting an epoxide and carbon dioxide with a metal complex of claim 1 to form a polycarbonate polymer composition; and ii. performing chromatography to obtain isolated polycarbonate polymer composition.

33. The method of claim 32, wherein the isolated polycarbonate polymer composition is pure.

34. The method of claim 32, wherein the isolated polycarbonate polymer composition is substantially free of the metal complex or any guanidine-containing portion thereof.

35. A method comprising the steps of:

i. contacting an epoxide and carbon dioxide with a metal complex of claim 1 to form a polycarbonate polymer composition; and ii. performing chromatography to obtain substantially isolated, intact metal complex.

* * * * *